United States Patent
Smith et al.

(10) Patent No.: US 7,078,218 B2
(45) Date of Patent: Jul. 18, 2006

(54) ALPHAVIRUS PARTICLES AND METHODS FOR PREPARATION

(75) Inventors: Jonathan F. Smith, Cary, NC (US); Kurt Kamrud, Apex, NC (US); Sergey Dryga, Chapel Hill, NC (US); Harold Alterson, Cary, NC (US); Jon Rayner, Apex, NC (US); Kim Butler, Cary, NC (US); Maureen F. Maughan, Durham, NC (US)

(73) Assignee: AlphaVax, Inc., Research Triangle Park, NC (US)

( * ) Notice: Subject to any disclaimer, the term of this patent is extended or adjusted under 35 U.S.C. 154(b) by 0 days.

(21) Appl. No.: 10/734,609

(22) Filed: Dec. 12, 2003

(65) Prior Publication Data

US 2004/0166573 A1    Aug. 26, 2004

Related U.S. Application Data

(60) Provisional application No. 60/433,058, filed on Dec. 13, 2002.

(51) Int. Cl.
| | |
|---|---|
| *C12N 7/00* | (2006.01) |
| *C12N 7/02* | (2006.01) |
| *C12N 15/00* | (2006.01) |
| *C12N 15/63* | (2006.01) |
| *C12N 15/87* | (2006.01) |

(52) U.S. Cl. ............... 435/235.1; 435/239; 435/320.1; 435/69.3; 435/455; 435/456; 435/457; 435/461

(58) Field of Classification Search ............ 424/199.1, 424/218.1; 435/239, 461, 235.1, 320.1, 69.3, 435/455, 456, 457
See application file for complete search history.

(56) References Cited

U.S. PATENT DOCUMENTS

| | | | |
|---|---|---|---|
| 4,650,764 A | 3/1987 | Temin et al. | |
| 4,708,871 A | 11/1987 | Geysen | |
| 5,091,309 A | 2/1992 | Schlesinger et al. | |
| 5,185,440 A | 2/1993 | Davis et al. | |
| 5,217,879 A | 6/1993 | Huang et al. | |
| 5,505,947 A | 4/1996 | Johnston et al. | |
| 5,639,650 A | 6/1997 | Johnston et al. | |
| 5,643,576 A | 7/1997 | Johnston et al. | |
| 5,703,057 A | 12/1997 | Johnston et al. | |
| 5,726,022 A | 3/1998 | Burmer | |
| 5,739,026 A | 4/1998 | Garoff et al. | |
| 5,766,602 A | 6/1998 | Xiong et al. | |
| 5,789,245 A | 8/1998 | Dubensky, Jr. et al. | |
| 5,792,462 A | 8/1998 | Johnston et al. | |
| 5,811,407 A | 9/1998 | Johnston et al. | |
| 5,814,482 A | 9/1998 | Dubensky, Jr. et al. | |
| 5,827,658 A | 10/1998 | Liang et al. | |
| 5,831,016 A | 11/1998 | Wang et al. | |
| 5,843,723 A | 12/1998 | Dubensky, Jr. et al. | |
| 5,853,719 A | 12/1998 | Nair et al. | |
| 5,958,738 A | 9/1999 | Lindemann et al. | |
| 5,989,553 A | 11/1999 | Johnston et al. | |
| 6,008,035 A | 12/1999 | Johnston et al. | |
| 6,015,686 A | 1/2000 | Dubensky, Jr. et al. | |
| 6,015,694 A | 1/2000 | Dubensky, Jr. et al. | |
| 6,146,874 A | 11/2000 | Zolotukhin et al. | |
| 6,156,558 A | 12/2000 | Johnston et al. | |
| 6,190,666 B1 | 2/2001 | Garoff et al. | |
| 6,194,191 B1 | 2/2001 | Zhang et al. | |
| 6,197,502 B1 | 3/2001 | Renner et al. | |
| 6,224,879 B1 | 5/2001 | Sjoberg et al. | |
| 6,242,259 B1 | 6/2001 | Polo et al. | |
| 6,261,570 B1 | 7/2001 | Parker et al. | |
| 6,267,967 B1 | 7/2001 | Johnston et al. | |
| 6,306,388 B1 | 10/2001 | Nair et al. | |
| 6,329,201 B1 | 12/2001 | Polo et al. | |
| 6,342,372 B1 | 1/2002 | Dubensky, Jr. et al. | |
| 6,376,236 B1 | 4/2002 | Dubensky, Jr. et al. | |
| 6,391,632 B1 | 5/2002 | Dubensky, Jr. et al. | |
| 6,426,196 B1 | 7/2002 | Dubensky, Jr. et al. | |
| 6,451,592 B1 | 9/2002 | Dubensky, Jr. et al. | |
| 6,485,958 B1 | 11/2002 | Blanch et al. | |
| 6,495,143 B1 | 12/2002 | Lee et al. | |
| 6,521,235 B1 | 2/2003 | Johnston et al. | |

(Continued)

FOREIGN PATENT DOCUMENTS

WO    WO 92/10578    6/1992

(Continued)

OTHER PUBLICATIONS

Pushko, P. et al. Replicon-Helper systems from attenuated Venezuelan equine encephalitis virus: expression of heterologous genes in vitro and immunization against heterologous pathogens in vivo (1997) Virology, vol. 239, pp. 389-401.*

(Continued)

*Primary Examiner*—James Housel
*Assistant Examiner*—M. Franco Salvoza

(57) ABSTRACT

Provided herein are methods for producing alphavirus replicon particles in high yield; replicon RNAs are electroporated into permissive cells, where the cells are at a relatively high density, together with at least one helper nucleic acid providing the necessary functions for packaging. After a growth period in appropriate medium, alphavirus replicon particles are harvested from the surfaces of the cells in which they were produced using a salt wash in which the salt concentration is from about 0.2 to about 5 M sodium chloride, calcium chloride, magnesium chloride, potassium chloride, ammonium acetate, ammonium bicarbonate, among others. After dilution, if necessary, the particles can be purified by a suitable chromatographic technique.

28 Claims, 6 Drawing Sheets

U.S. PATENT DOCUMENTS

Figure 1:
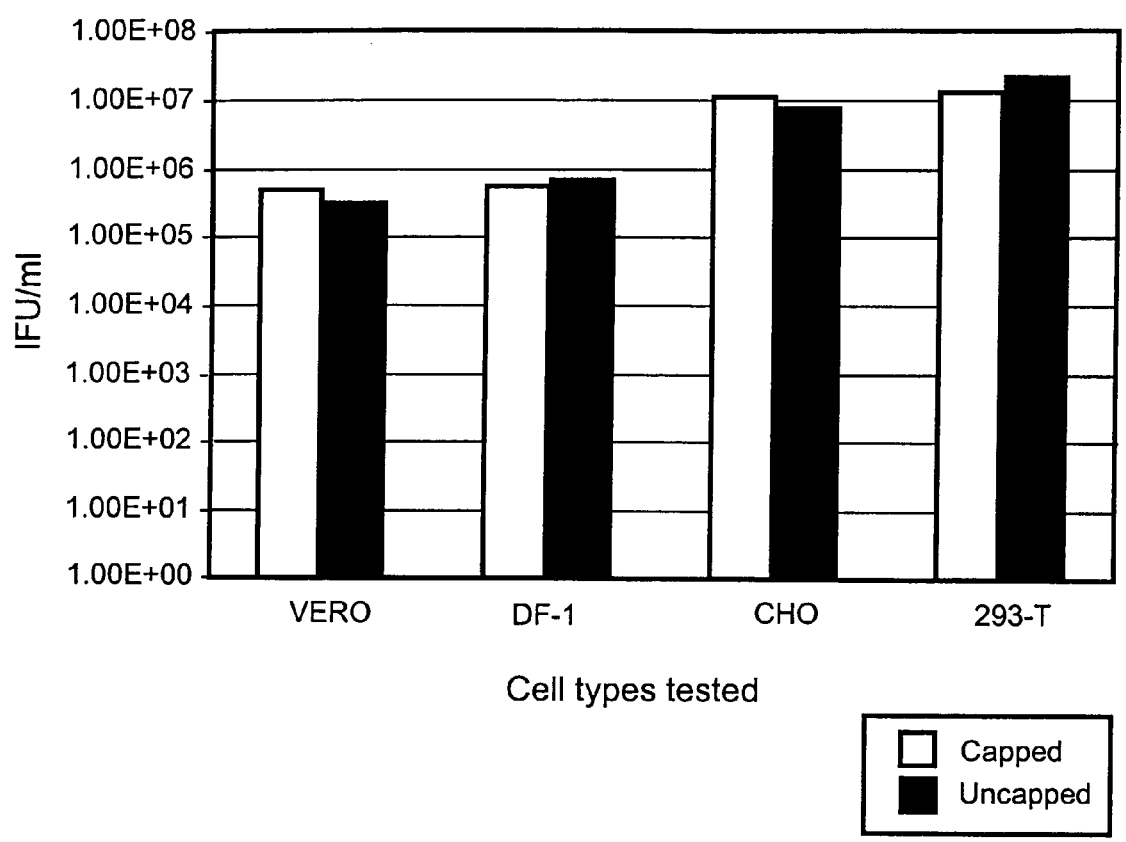
Figure 2:
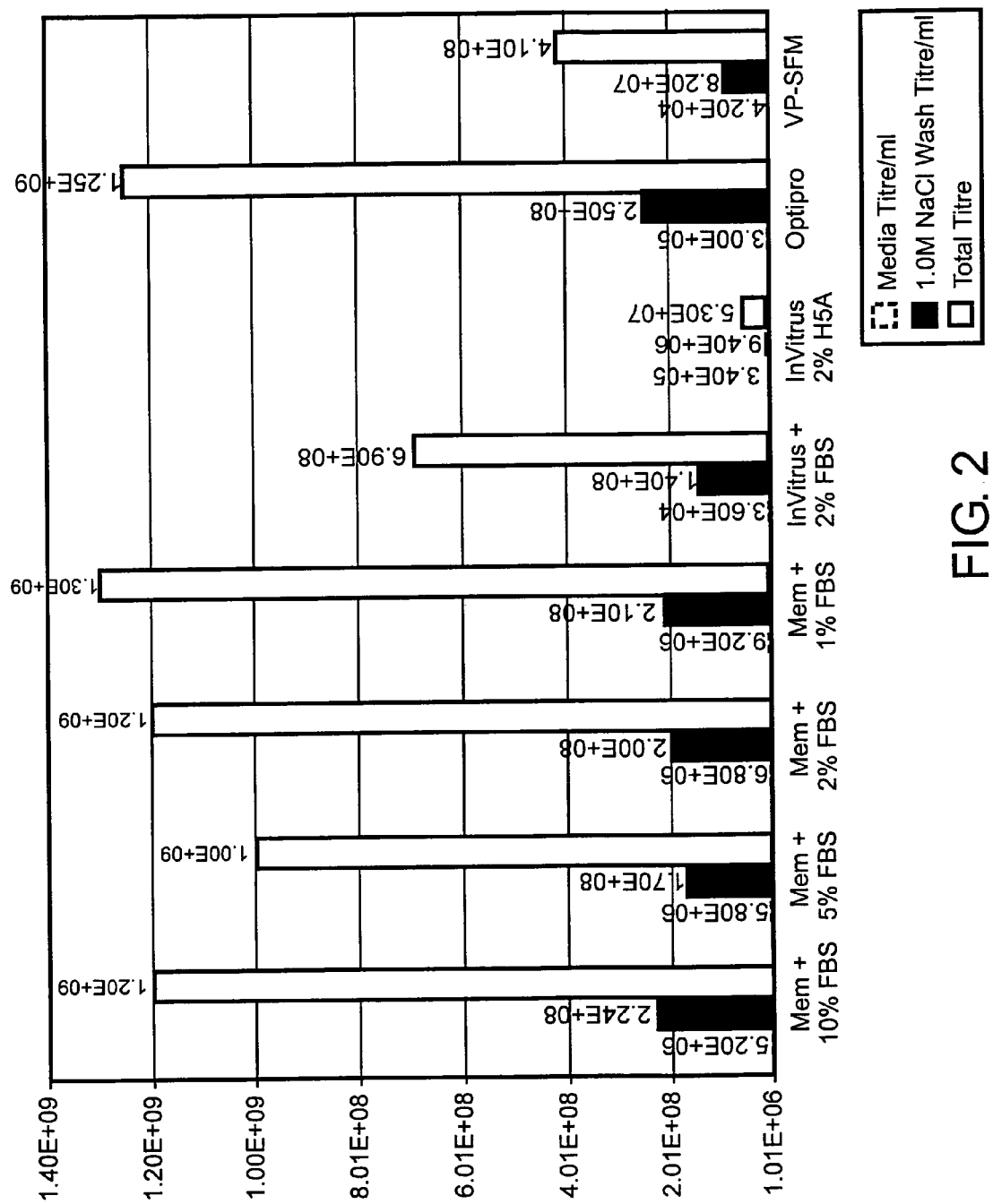

| | | |
|---|---|---|
| 6,583,121 B1 | 6/2003 | Johnston et al. |
| 6,767,699 B1 | 7/2004 | Polo et al. |
| 6,770,283 B1 | 8/2004 | Garoff et al. |
| 6,783,939 B1 | 8/2004 | Olmsted et al. |
| 6,844,188 B1 | 1/2005 | MacDonald et al. |
| 2002/0018766 A1 | 2/2002 | Roberts et al. |
| 2002/0102273 A1 | 8/2002 | Grieve et al. |
| 2002/0141975 A1 | 10/2002 | Olmsted et al. |
| 2003/0021766 A1 | 1/2003 | Vadjy et al. |
| 2003/0091591 A1 | 5/2003 | Xiong et al. |
| 2003/0119182 A1 | 6/2003 | Smith et al. |
| 2003/0148262 A1 | 8/2003 | Polo et al. |
| 2003/0232035 A1 | 12/2003 | Dubensky et al. |
| 2004/0029278 A1 | 2/2004 | Dubensky et al. |
| 2004/0166573 A1 | 8/2004 | Smith et al. |
| 2004/0235133 A1 | 11/2004 | Frolov et al. |
| 2005/0054107 A1 | 3/2005 | Chulay et al. |
| 2005/0123555 A1 | 6/2005 | Olmsted et al. |

FOREIGN PATENT DOCUMENTS

| | | |
|---|---|---|
| WO | WO 95/27044 | 10/1995 |
| WO | WO 95/31565 | 11/1995 |
| WO | WO 96/17072 | 6/1996 |
| WO | WO 96/37220 | 11/1996 |
| WO | WO 96/37616 | 11/1996 |
| WO | WO 99/07834 * | 2/1999 |
| WO | WO 99/08706 | 2/1999 |
| WO | WO 00/39318 | 7/2000 |
| WO | WO 00/61772 | 10/2000 |
| WO | WO 02/20721 | 3/2002 |
| WO | WO 03/023026 A | 3/2003 |
| WO | WO 04/085660 | 10/2004 |

OTHER PUBLICATIONS

Polo, J.M. et. al. Stable alphavirus packaging cell lines for Sindbis virus- and Semliki forest virus-derived vectors (1999) Proc. Natl. Acad. Sci. vol. 96, pp. 4598-4603.*

Lijestrom, P. et. al. In vitro mutagenesis of a full-length CDNA clone of Semliki Forest virus: the small 6,000-molecular weight membrane protein modulates virus release (1991) J. Virol. 65:4107-4113.*

Rayner, J.O. et. al. Alphavirus vectors and vaccination (2002) Rev. Med. Virol. 12:279-296.*

Bell, J.W. et. al. Effect of low-NaCl medium of the envelope glycoproteins of Sindbis virus (1978) Journal of Virology, vol. 25(3), pp. 764-769.*

Bredenbeek, P.J. et. al. Sindbis virus expression vectors: Packaging of (1993) J. Virol. 67(11) pp. 6439-6446.*

Technical Bulletin No. 166: RiboMAX Large Scale RNA Production Systems—SP6 and T7; Promega Corporation; pp. 1-11; Revised Sep. 2001—On http://www.promega.com/tbs/tb166/tb166.pdf on Nov. 4, 2004.*

Balasuriya et al. (Feb. 2002) "Alphavirus replicon particles expressing the two major envelope proteins of equine arteritis virus induce high level protection against challenge with virulent virus in vaccinated horses"; Vaccine 20:1609-1617.

Bell et al. (Mar. 1978) "Effect of Low-NaCl Medium on the Envelope Glycoproteins of Sindbis Virus"; J. Virol. 25(3):764-769.

Bernard et al. (2000) "Mutations in the E2 Glycoprotein of Venezuelan Equine Encephalitis Virus Confer Heparan Sulfate Interaction, Low Morbidity, and Rapid Clearance from Blood of Mice," Virology 276:93-103.

Casimiro et al. (Jan. 2002) "Vaccine-induced immune responses in rodents and nonhuman primates by use of a humanized immunodeficiency virus type 1 pol gene"; J. Virol. 76:185-195.

Davies et al. (1991), "Attenuating Mutations in the E2 Glycoprotein Gene of Venezuelan Equine Encephalitis Virus: Construction of Single and Multiple Mutants in a Full-Length cDNA Clone," Virology 183:20-31.

Davies et al. (1986) "A Single Nucleotide Change in the E2 Glycoprotein Gene of Sindbis Virus Affects Penetration Rate in Cell Culture and Virulence in Neonatal Mice," Proc. Natl. Acad. Sci. USA 83:6771-6775.

Frolov et al. (1996) "Alphavirus-based expression vectors: Strategies and applications"; Proc. Natl. Acad. Sci.USA 93:11371-11377.

Geisbert et al. (May 2002) "Evaluation in Nonhuman Primates of Vaccines against Ebola Virus"; Emerging Infect. Dis. 8(5):503-507.

Golzio et al. (Jun. 2002) "Cell Synchronization Effect on Mammalian Cell Permeabilization and Gene Delivery by Electronic Field," Biochim. Biophys. Acta 1563:23-28.

Hahn et al. (1992) "Infectious Sindbis Virus Transient Expression Vectors for Studying Antigen Processing and Presentation," Proc. Natl. Acad. Sci. USA 89:2679-2683.

Heiser et al. (Feb. 2002) "Autologous dendritic cells transfected with prostate-specific antigen RNA stimulate CTL responses against metastatic prostate tumors," J. Clin. Inv. 109(3):409-417.

Hevey et al. (1998) "Marburg Virus Vaccines Based upon Alphavirus Replicons Protect Guinea Pigs and Nonhuman Primates"; Virology 251:28-37.

Hill et al., (1997) "RNA-RNA recombination in Sindbis virus: role of the 3' conserved motif, poly(A) tail, and nonviral sequences of template RNAs in polymerase recognition and template switching," J. Virol. 71:2693-2704.

Johnston et al., (1988) "Selection for Accelerated Penetration in Cell Culture Coselects for Attenuated Mutants of Venezuelan Equine Encephalitis Virus," Virology 162:437-443.

Kinney et al. (1989) "The Full Length Nucleotide Sequences of the Virulent Trinidad Donkey Strain of Venezuelan Equine Encephalitis Virus and Its Attenuated Vaccine Derivative, Strain TC-83," Virology 170:19-30.

Klimstra et al., (1998) "Adaptation of Sindbis Virus to BHK Cells Selects for Use of Heparan Sulfate as an Attachment Receptor," J. Virol 72:7357-7366.

Koller et al. (Sep. 2001) "A high-throughput alphavirus-based expression cloning system for mammalian cells"; Nature Biotech. 19:851-855.

Kumamoto et al. (Jan. 2002) "Induction of Tumor-Specific Protective Immunity by In situ Langerhans Cell Vaccine," Nature Biotech. 20:64-69.

Liljestrom et al. (1991) "In Vitro Mutagenesis of a Full-Length cDNA Clone of Semliki Forest Virus: The Small 6,000-Molecular-Weight Membrane Protein Modulates Virus Release," J. Virol. 65:4107-4113.

Lu et al., (Jan. 2001) "Transmission of Replication-Defective Sindbis Helper Vectors Encoding Capsid and Envelope Proteins," J. Virol. Methods 91(1):59-65.

Olmsted et al. (1986) "Characterization of Sindbis Virus Epitopes Important for Penetration in Cell Culture and Pathogenesis in Animals," Virology 148:245-254.

Pushko et al. (1997) "Replicon-Helper systems from Attenuated Venezuelan Equine Encephalitis Virus: Expression of Heterologous Genes in Vitro and Immunization against Heterologous Pathogens in Vivo"; Virology 239:389-401.

Waite et al. (Jan. 1970) "Inhibition of Sindbis Virus Production by Media of Low Ionic Strength: Intracellular Events and Requirements for Reversal"; *J. Virol.* 5:60-71.

Ward et al. (Jun. 2002) "Immunotherapeutic Potential of Whole Tumor Cells," *Cancer Immunol. Immunother.* 51:351-357.

Wilson et al. (Jul. 2001) "Vaccine Potential of Ebola Virus VP24, VP30, VP35, and VP40 Proteins"; *Virology* 286:384-390.

Yamanaka et al. (Sep. 2002) Marked enhancement of anti-tumor immune responses in mouse brain tumor models by genetically modified dendritic cells producing Semliki Forest virus-mediated interleukin-12; *J. Neurosurg.* 97:611-618.

Yamanaka et al. (Mar. 2001) "Enhancement of antitumor immune response in glioma models in mice by genetically modified dendritic cells pulsed with Semliki Forest virus-mediated complementary DNA"; *J. Neurosurg.* 94:474-481.

Ying et al. (1999) "Cancer Therapy Using a Self-Replicating RNA Vaccine," *Nature Medicine* 5(7):823-827.

Barouch et al. (2000) "Augmentation of Immune Responses to HIV-1 and Simian Immunodeficiency Virus DNA Vaccines by IL-2/Ig Plasmid Administration in Rhesus Monekeys," *Proc. Natl. Acad. Sci. USA* 97(8):4192-4197.

Berglund et al. (1993) "Semliki Forest Virus Expression System: Production of Conditionally Infectious Recombinant Particles," *Bio/Technology* 11:916-920.

Betts et al. (1997) "Cross-Clade Human Immunodeficiency Virus (HIV)-Specific Cytotoxic T-Lymphocyte Responses in HIV-Infected Zambians," *J. Virol.* 71(11):8908-8911.

Bredenbeek et al. (1993) "Sindbis Virus Expression Vectors: Packaging of RNA Replicons by Using Defective Helper RNAs," *J. Virol.* 67:6439-6446.

Caley et al. (1997) "Humoral, Mucosal, and Cellular Immunity in Response to a Human Immunodeficiency Virus Type 1 Immunogen Expressed by a Venezuelan Equine Encephalitis Virus Vaccine Vector," *J. Virol.* 71(4):3031-3038.

Caley et al. (1999) "Venezuelan Equine Encephalitis Virus Vectors Expressing HIV-1 Proteins: Vector Design Strategies for improved Vaccine Efficacy," *Vaccine* 17:3124-3135.

Chappell et al. (Feb. 2000) "A 9-nt Segment of a Cellular mRNA can Function as an Internal Ribosome Site (IRES) and When Present in Linked Vaccine Efficacy," *Proc. Natl. Acad. Sci. USA* 97(4):1536-1541.

Corsini et al. (1996) "Efficiency of Transduction by Recombinant Sindbis Replicon Virus Varies Among Cell Lines, Includiing Mosquito Cells and Rat Sensory Neurons," *BioTechniques* 21(3):492-497.

Cutler et al. (1986) "Mutants of the Membrane-binding Region of Semliki Forest Virus E2 Protein.I. Cell Surface Transport and Fusogenic Activity," *J. Cell Biol.* 102:889-901.

Davis et al. (1993) "A Genetically Engineered Live Virus Vaccine for Venezuelan Equine Encephalitis," *J. Cell Biochem.* Supp O No. 17 part D, Abstract N404.

Davis et al. (1996) "A Viral Vaccine Vector that Expresses Foreign Genes in Lymph Nodes and Protects Against Mucosal Challenge," *J. Virol.* 70:3781-3787.

Davis et al. (1995) "Attenuated Mutants of Venezuelan Equine Encephalitis Virus Containing Lethal Mutations in the PE2 Cleavage Signal Combined with a Seond-Site Suppressor Mutation in E1," *Virol.* 212:102-110.

Davis et al. (1991) "Attenuating Mutations in the E2 Glycoprotein Gene of Venezuelan Equine Encephalitis Virus: Construction of Single and Multiple Mutants in a Full-Length cDNA Clone," *Virol.* 183:20-31.

Davis et al. (1996) "Immunization Against Influenza with Attenuated Venezuelan Equine Encephalitis Virus Vectors," In: *Options for the Control of Influenza III*, L.E.Brown and A.W.Hampson, eds. Elsevier, Amsterdam pp. 803-809.

Davis et al. (1990) "*In Vitro* Synthesis of Infectious Venezuelan Equine Encephalitis Virus RNS from a cDNA Clone: Analysis of a Viable Deletion Mutant and Mutations Affecting Virulence," *Vaccines* 90:109-113.

Davis et al. (1989) "In Vitro Synthesis of Infectious Venezuelan Equine Encephalitis Virus RNA from a cDNA Clone: Analysis of a Viable Deletion Mutant," *Virol.* 171:189-204.

Davis et al. (2001) "Vaccination of Macaques Against Pathogenic Simian Immunodeficiency Virus with Venezuelan Equine Encephalitis Virus Replicon Particles," *J. Virol.* 74(1):371-378.

Davis et al. (1994) "A Molecular Genetic Approach to the Study of Venezuelan Equine Encephalitis Virus Pathogenesis," *Arch. Virol.* 9:99-109.

Dubensky et al. (1996) "Sindbis Virus DNA-Based Expression Vectors: Utility for in Vitro and in Vivo Gene Transfer," *J. Virol.* 70:508-519.

Dubuisson et al. (1993) "Sindbis Virus Attachment: Isolation and Characterization of Mutants With Impaired Binding to Vertebrate Cells," *J. Virol.* 67:3363-3374.

Favre et al. (1993) "Semliki Forest Virus Capsid Protein Expressed by a Baculovirus Recombinant," *Arch. Virol.* 132:307-319.

Feyzi et al (1997) "Structural Requirement of Heparan Sulfate for Interaction with Herpes Simplex Virus Type 1 Virions and Isolated Glycoprotein C," *J. Biol. Chem.* 272(40):24850-24857.

Garoff et al. (1983) "Expression of Semliki Forest Virus Proteins from Cloned Complementary DNA. II. The Membrane-Spanning Glycoprotein E2 is Transported to the Cell Surface Without its Normal Cytoplasmic Domain," *J. Cell Biol.* 97:652-658.

Geigenmuller-Gnirke et al. (1991) "Complementation Between Sindbis Viral RNAs Produce infectious Particles with a Bipartite Genome," *Proc. Natl. Acad. Sci. USA.* 88:3253-3257.

Gingras et al. (1996) "Activation of the Translational Suppressor 4E-BP1 Following Infection with Encephalomyocarditis Virus and Poliovirus," *Proc. Natl. Acad. Sci. USA* 93:5578-5583.

Gradi et al. (1998) "Proteolysis of Human Eukaryotic Translation Initiation Factor ElF4GII, But Not elF4GI, Coincides with the Shutoff of Host Protein Synthesis after Poliovirus Infection," *Proc. Natl. Acad. Sci. USA* 95:11089-11094.

Grieder et al. (1995) "Specific Restrictions in the Progression of Venezuelan Equine Encephalitis Virus-Induced Disease Resulting from Single Amino Acid Changes in Glycoproteins," *Virol.* 206:994-1006.

Heidner et al. (1994) "Lethality of PE2 Incorporation into Sindbis Virus can be Suppressed by Second-Site Mutations in E3 and E2," *J. Virol.* 68:2683-2692.

Heise et al. (Jan. 2003) "An Attenuation Mutation in nsP1 of the Sindbis-Group Virus S.A.AR86 Accelerates Nonstructural Protein Processing and Up Regulates Viral 26S RNA Synthesis," *J. Virol.* 77(2):1149-1156.

Herweijer et al. (1997) "Self-Amplifying Vectors for Gene Delivery," *Adv. Drug Rev.* 27:5-16.

Hevey et al. (Nov. 2001) "Marburg Virus Vaccines: Comparing Classical and New Approaches," *Vaccine* 20:586-593.

Hirsch et al. (1996) "Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara," *J. Virol.* 7096):3741-3752.

Hodgson et al. (1993) "Expression of Venezuelan Equine Encephalitis Viral Proteins by Recombinant Baculoviruses," *Am. J. Trop. Med. Hygiene* 49:195-196.

Holcik et al. (2000) "Functional Characterization of the X-Linked Inhibitor of Apoptosis (XIAP) Internal Ribosome Entry Site Element: Role of La Autoantigen in XIAP Translation," *Mol. Cell. Biol.* 20(13):4648-4657.

Holcik et al. (1999) "A New Internal-Ribosome-Entry-Site Motif Potentiates XIAP-Mediated Cytoprotection," *Nature Cell Biol.* 1:190-192.

Holcik et al. (Jan. 2003) "The Internal Ribosome Entry Site-Mediated Translation of Antiapoptotic Protein XIAP is Modulated by the Heterogeneous Nuclear Ribonucleoproteins C1 and C2," *Mol. Cell. Biol.* 23(1):280-288.

International Search Report of International Application Serial No. PCT/US02/28610 filed Sep. 6, 2002.

International Search Report Corresponding to PCT/US 2004/008458 Filed Oct. 25, 2004.

Jalanko (1985) "Expression of Semliki Forest Virus Capsid Protein from SV40 Recombinant Virus," *FEBS Lett.* 186:59-64.

Jang et al. (1990) "Cap-Independent Translation of Encephalomyocarditis Virus RNA: Structural Elements of the Internal Ribosomal Entry Site and Involvement of a Cellular 57kD RNA-Binding Protein," *Genes and Development* 4:1560-1572.

Joachims et al. (1999) "Cleavage of Poly(A)-Binding Protein by Enterovirus Proteases Concurrent with Inhibition of Translation In Vitro," *J. Virol.* 73(1):718-727.

Johnston et al. (1996) "Alphaviruses,", In: *Fields Virology*, 3rd ed., Lippincott-Raven Publishers, Philadelphia, Chapt 28:843-898.

Johnston et al. (1988) "Selection for Accelerated Penetration in Cell Culture Coselects for Attenuated Mutants of Venezuelan Equine Encephalitis Virus," *Virol.* 162:437-443.

Kinney et al. (1993) "Attenuation of Venezuelan Equine Encephalitis Virus Strain TC-83 Is Encoded by the 5'-Noncoding Region and the E2 Envelope Glycoprotein," *J. Virol.* 67:1269-1277.

Knight (1999) "Secretion from Bovine Chromaffin Cells Acutely Expressing Exogenous Proteins using a Recombinant Semliki Forest Virus Containing an EGFP Reporter," *Mol. Cell. Neuro.* 14(6):486-505.

Kohl et al. (1999) "Transient Gene Expression in Mammalian and Mosquito Cells Using a Recombinant Semliki Forest Virus Expressing T7 RNA Polymerase," *Appl. Microbiol. Biotechnol.* 53(1):51-56.

Kondor-Koch et al. (1983) "Expression of Semliki Forest Virus Proteins from Cloned Complementary DNA. I. The Fusion Activity of the Spike Glycoprotein," *J. Cell. Biol.* 97(3):644-651.

Lee et al. (1997) "Efficient Long-Term Coexpression of a Hammerhead Ribozyme Targeted to the U5 Region of HIV-1 LTR by Linkage to the Multidrug-Resistance Gene," *Antisense & Nuclei Acid Drug Developments* 7:511-522.

Lemm et al. (1994) "Polypeptide Requirements for Assembly of Functional Sindbus Virus Replication Complexes: A Model for the Temporal Regulation of Minus-and Plus-Strand RNA Synthesis," *EMBO J.* 13:2925-2934.

Leone et al. (1985) "In Vitro Synthesis of the Gene Coding for the Glycoprotein E1 of Sindbis Virus," *Microbiologica* 8(2):123-130.

Li et al. (1996) "Production of Infectious Recombinant Moloney Murine Leukemia Virus Particles in BHK Cells Using Semliki Forest Virus-Derived RNA Expression Vectors," *Proc. Natl. Acad. Sci. USA* 93:11658-11663.

Liljestrom et al. (1991) "A New Generation of Animal Cell Expression Vectors Based on the Semliki Forest Virus Replicon." *BioTechnology* 9:1356-1361.

Liljestrom (1994) "Alphavirus Expression Systems," *Curr. Opin. Biotechnol.* 5:495-500.

Lobigs et al. (1990) "Fusion Function of the Semliki Forest Virus Spike is Activated by Proteolyic Cleavage of the Envelope Glycoprotein Precursor p62," *J. Virol.* 64:1233-1240.

Lundstrom et al. (1985) "Secretion of Semliki Forest Virus Membrane Glycoprotein E1 from *Bacillus subtilis,*" *Virus Res.* 2:69-83.

Martinez-Salas et al. (May 2001) "Functional Interactions in Internal Translation Initiation Directed by Viral and Cellular IRES Elements," *J. Gen. Virol.* 82:973-984.

McKnight et al. (1996) "Deduced Consensus Sequence of Sindbis Virus Strain AR339: Mutations Contained in Laboratory Strains which Affect Cell Culture and In Vivo Phenotypes," *J. Virol.* 70(3):1981-1989.

Melancon et al. (1987) "Processing of the Semliki Forest Virus Structural Polyprotein: Role of Capsid Protease," *J. Virol.* 61:1301-1309.

Melancon et al. (1986) "Reinitiation of Translocation in the Semliki Forest Virus Structural Polyprotein: Identification of the Signal for the E1 Glycoprotein," *EMBO J.* 5:1551-1560.

Morgenstern et al. (1990) "Advanced Mammalian Gene Transfer: High Titre Retroviral Vectors with Multiple Drug Selection Markers and a Complementary Helper-Free Packaging Cell Line," *Nuc. Acid. Res.* 18:3587-3596.

Oker-Blom et al. (1989) "Expression of Sindbis Virus 26S cDNA in *Spodoptera frugiperda* (Sf9) Cells, Using a Baculovirus Expression Vector," *J. Virol.* 63:1256-1264.

Orkin et al. (1995) "Report and Recommendations of the Panel to Assess the NIH Investment in Research on Gene Therapy".

Paredes et al. (1993) "Three-Dimensional Structure of a Membrane-Containing Virus," *Proc. Natl. Acad. Sci. USA* 90:9095-9099.

Polo et al. (1990) "Attenuating Mutations in Glycoproteins E1 and E2 of Sindbis Virus Produces a Highly Attenuated Strain When Combined in Vitro," *J. Virol.* 64:4438-4444.

Presley et al. (1991) "Proteolytic Processing of the Sindbis Virus Membrane Protein Precursor PE2 is Nonessential for Growth in Vertebrate Cells but is required for Efficient Growth in Invertebrate Cells," *J. Virol.* 65:1905-1909.

Pugachev et al. (2000) "Development of a Rubella Virus Vaccine Expression Vector: Use of a Picornavirus Internal Ribosome Entry Site Increases Stability of Expression," *J. Virol.* 74:10811-10815.

Pushko et al. (Dec. 2001) "Individual and Bivalent Vaccines Based on Alphavirus Replicons Protect Guinea Pigs Against Infection with Lassa and Ebola Viruses," *J. Virol.* 75(23):11677-11685.

Pushko et al. (1997) "Replicon-Helper Systems from Attenuated Venezuelan Equine Encephalitis Virus: Expression of Heterologous Genes in Vitro and Immunization Against Heterologous Pathogens in Vivo," *Virol.* 239:389-401.

Rayner et al. (Sep. 2002) "Alphavirus Vectors and Vaccination," *Rev. Med. Virol.* 12(5):279-296.

Rice et al. (1985) "Expression of Sindbis Virus Structural Proteins via Recombinant Vaccinia Virus: Synthesis, Processing, and Incorporation into Mature Sindbis Virions," *J. Virol.* 56:227-239.

Riedel (1985) "Different Membrane Anchors Allow the Semliki Forest Virus Spike Subunit E2 to Reach the Cell Surface," *J. Virol.* 54:224-228.

Roberts et al. (1997) "Complementation of Defective Picornavirus Internal Ribosome Entry Site (IRES) Elements by the Coexpression of Fragments of the IRES," *Virol.* 227:53-62.

Russell et al. (1989) "Sindbis Virus Mutations Which Coordinately Affect Glycoprotein Processing, Penetration, and Virulence in Mice," *J. Virol.* 63:1619-1629.

Salminen et al. (1992) "Membrane Fusion Process of Semliki Forest Virus II: Cleavage-Dependent Reorganization of the Spike Protein Complex Controls Virus Entry," *J. Cell. Biol.* 116:349-357.

Schlesinger et al. (1996) "*Togaviridae*: The Viruses and Their Replication," In: *Fields Virology*, 3$^{rd}$ Edition, Lipincott-Raven Publishers, Philadelphia, pp. 825-841.

Schlesinger et al. (1994) "Recombination Between Sindbis Virus RNAs," *J. Virol.* 65:4017-4025.

Schoepp et al. (1993) "Directed Mutagenesis of a Sindbis Virus Pathogenesis Site," *Virol.* 193:149-159.

Shi et al. (May 2002) "Construction and Characterization of Subgenomic Replicons of New York Strain of West Nile Virus," *Virol.* 296(2):219-233.

Simpson et al. (1996) "Complete Nucleotide Sequence and Full Length cDNA Clone of S.A.Ar86, a South African Alphavirus Related to Sindbis," *Virol.* 222:464-469.

Sjoberg et al. (1994) "A Significantly Improved Semliki Forest Virus Expression System Based on Translation Enhancer Segments from the Viral Capsid Gene," *BioTechnol.* 12:1127-1131.

Strauss et al. (1990) "Alphavirus Proteinases," *Sem. Virol.* 1:347-356.

Strauss et al. (1994) "The Alphaviruses: Gene Expression, Replication, and Evolution," *Microbiological Rev.* 58:491-562.

Suomalainen et al. (1992) "Spike Protein-Nucleocapsid Interactions Drive the Budding of Alphaviruses," *J. Virol.* 66(8):4737-4747.

Sykes et al. (1999) "Genetic Live Vaccines Mimic the Antigenicity but Not Pathogenicity of Live Viruses," *DNA Cell Biol.* 18(7):521-531.

Thompson et al. (Oct. 2003) "Enterovirus 71 Contains a Type I IRES Element that Functions When Eukaryotic Initiation Factor elF4G is Cleaved," *Virol.* 315:259-266.

Ubol et al. (1994) "Neurovirulent Strains of Alphavirus Induce Apoptosis in bcl-2-Expressing Cells: Role of A Single Amino Acid Change in the E2 Glycoprotein," *Proc. Natl. Acad. Sci. USA* 91:5202-5206.

Van der Velden et al. (1995) "Defective Point Mutant of the Encephalomyocarditis Virus Internal Ribosome Entry Site can be Complemented *in Trans*," *Virol.* 214:82-90.

Verma et al. (1997) "Gene Therapy—Promise and Prospects," *Nature* 389:239-242.

Wang et al. (2000) "Core Protein-Coding Sequence, But No Core Protein, Modulates the Efficiency of Cap-Independent Translation Directed by the Internal Ribosome Entry Site of Hepatitis C Virus," *J. Virol.* 74(23):11347-11358.

Weiss et al. (1991) "Recombination Between Sindbis Virus RNAs," *J. Virol.* 65:4017-4025.

Wen et al. (1986) "Expression of Genes Encoding Vesicular Stomatitis and Sindbis Virus Glycoproteins in Yeast Leads to Formation of Disulfide-Linked Oligomers," *Virol.* 153:150-154.

Wen et al. (2001) "Tricistronic Viral Vectors Co-Expressing Interleukin-12 (IL-12) and CD80 (B7-1) for the Immunotherapy of Cancer: Preclinical Studies in Myeloma," *Cancer Gene Therapy* 8(5):361-370.

Williamson et al. (Feb. 2003) "Characterization and Selection of HIV-1 Subtype C Isolates for Use in Vaccine Development," *AIDS Research and Human Retroviruses* 19(2):133-144.

Wilson et al. (2000) "Naturally Occurring Dicistronic Cricket Paralysis Virus RNA is Regulated by Two Internal Ribosome Entry Sites," *Mol. Cell. Biol.* 20(14):4990-4999.

Xiong et al. (1989) "Sindbis Virus: An Efficient, Broad Host Range Vector for Gene Expression in Animal Cells," *Science* 243:1188-1191.

Yang et al. (1997) "Location of the Internal Ribosome Entry Site in the 5'Non-Coding Region of the Immunoglobulin Heavy-Chain Biinding Protein (BiP) mRNA: Evidence for Specific RNA-Protein Interactions," *Nuc. Acids. Res.* 25(14):2800-2807.

Zhao et al. (1992) "Role of Cell Surface Spikes in Alphavirus Budding," *J. Virol.* 66:7089-7095.

\* cited by examiner

Different Salt Compositions for the Release Medium

ALPHAVIRUS PARTICLES AND METHODS FOR PREPARATION

CROSS REFERENCE TO RELATED APPLICATIONS

This application claims benefit of U.S. Provisional Application 60/433,058 filed Dec. 13, 2002, which is incorporated by reference herein to the extent there is no inconsistency with the present disclosure.

ACKNOWLEDGMENT OF FEDERAL RESEARCH SUPPORT

Not applicable.

BACKGROUND OF THE INVENTION

The present invention relates to recombinant DNA technology, and in particular to introducing foreign nucleic acid(s) in a eukaryotic cell, and more particularly to methods for producing infective virus particles or virus-like particles in high yields, especially particles useful in immunotherapies and/or gene therapy applications. In particular, the present invention discloses a high-yielding, GMP-compatible, commercially feasible process for producing highly purified alphavirus replicon particle (ARP) preparations suitable for use in human and veterinary medicine.

The Alphavirus genus includes a variety of viruses, all of which are members of the Togaviridae family. The alphaviruses include Eastern Equine Encephalitis Virus (EEE), Venezuelan Equine Encephalitis Virus (VEE), Everglades Virus, Mucambo Virus, Pixuna Virus, Western Equine Encephalitis Virus (WEE), Sindbis Virus, Semliki Forest Virus, Middleburg Virus, Chikungunya Virus, O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, and Buggy Creek Virus. The viral genome is a single-stranded, messenger-sense RNA, modified at the 5'-end with a methylated cap and at the 3'-end with a variable-length poly (A) tract. Structural subunits containing a single viral protein, capsid, associate with the RNA genome in an icosahedral nucleocapsid. In the virion, the capsid is surrounded by a lipid envelope covered with a regular array of transmembrane protein spikes, each of which consists of a heterodimeric complex of two glycoproteins, E1 and E2. See Pedersen et al., *J. Virol* 14:40 (1974). The Sindbis and Semliki Forest viruses are considered the prototypical alphaviruses and have been studied extensively. See Schlesinger, The Togaviridae and Flaviviridae, Plenum Publishing Corp., New York (1986). The VEE virus has been studied extensively, see, e.g., U.S. Pat. No. 5,185,440.

The studies of these viruses have led to the development of techniques for vaccinating against the alphavirus diseases and against other diseases through the use of alphavirus vectors for the introduction of foreign genes. See U.S. Pat. No. 5,185,440 to Davis et al., and PCT Publication WO 92/10578. The use of alphavirus vectors to direct the expression of foreign genes in eukaryotes has become a topic of increasing interest. It is well known that live, attenuated viral vaccines are among the most successful means of controlling viral disease. However, for some virus pathogens, immunization with a live virus strain may be either impractical or unsafe. One alternative strategy is the insertion of sequences encoding immunizing antigens of such agents into a live, replicating strain of another virus. One such system utilizing a live VEE vector is described in U.S. Pat. Nos. 5,505,947 and 5,643,576 to Johnston et al. Another such system is described by Hahn et al., *Proc. Natl. Acad. Sci. USA* 89:2679–2683 (1992), wherein Sindbis virus constructs express a truncated form of the influenza hemagglutinin protein. Another system is the alphavirus replicon system, as described in U.S. Pat. No. 6,190,666 to Garoff et al., U.S. Pat. Nos. 5,792,462 and 6,156,558 to Johnston et al., U.S. Pat. Nos. 5,814,482, 5,843,723, 5,789,245, 6,015,694, 6,105,686 and 6,376,236 to Dubensky et al; U.S. Pat. No. 6,767,699 (Polo et al.), U.S. Pat. No. 6,521,235 (Johnston et al.), Frolov et al. (1996) *Proc. Natl. Acad. Sci. USA* 93:11371–11377 and Pushko et al. (1997) *Virology* 239:389–401.

Accordingly, there remains a need in the art for methods, which allow the production of infective, highly immunogenic alphavirus particles and derivatives thereof in high purity and in high yield, especially for use in vaccine preparations of high purity.

SUMMARY OF THE INVENTION

The present invention provides a high-yielding, GMP-compatible, commercially feasible process for producing highly purified alphavirus replicon particle (ARP) or virus preparations suitable for use in human and veterinary medicine. The present invention is also applicable to the production of live attenuated alphavirus vaccines and immunogenic compositions containing same, which attenuated alphavirus may or may not carry heterologous genes for expression in the vaccinee, as described in U.S. Pat. No. 5,643,576. The method of the present invention comprises the steps of (a) introducing an alphaviral replicon nucleic acid (or an alphavirus nucleic acid) into a host cell, wherein said replicon nucleic acid contains at least an alphavirus packaging signal and at least one coding sequence for a gene(s) of interest expressible in said alphaviral replicon nucleic acid, wherein the host cell is capable of expressing alphavirus structural proteins required to produce ARPs, to produce a modified host cell; (b) culturing said modified host cell in a medium under conditions allowing expression of the structural proteins and replication of the alphaviral replicon nucleic acid, and then packaging of the alphaviral replicon nucleic acid to form ARPs; (c), optionally separating the modified host cells from the medium, and (d) after step (b) or (c) contacting the modified host cells with an aqueous solution having an ionic strength of at least approximately 0.20 M, or from about 0.2 M to about 5 M, (herein the "Release Medium") to release the ARPs into the aqueous solution to produce an ARP-containing solution. The ionic strength of the Release Medium can be achieved using salts which do not inactivate the virions or ARPs, and suitable salts include, but are not limited to, sodium chloride, magnesium chloride, ammonium chloride, ammonium acetate, potassium chloride, calcium chloride and ammonium bicarbonate. Advantageously, the Release Medium (salt wash) comprises a buffer with a pH from about 6 to about 9, desirably from about 6.5 to about 8.5. Where the cells are not separated from the medium, the ionic strength of the medium can be raised by the addition of a solid salt or a concentrated salt solution to provide the increased ionic strength for releasing the ARPs (or virions) from the cells. The salt wash of the producing cells with Release Medium appears to improve ARP recovery, especially when there are particular surface charges on the ARP surface; in the case of VEE, the amino acid residues at E2-209 and/or E2-120 appear to provide good sites for introducing a positive charge. Amino acid substitutions resulting in charge changes in certain attenuated virus mutants improve salt wash recovery of ARPs. 16 mM sodium phosphate, 0.5 M NaCl is an exemplary Release Medium used in the salt wash.

The ARPs or virus particles are produced in a cell that allows packaging of the virus or replicon nucleic acid into infective particles, i.e., in an alphavirus-permissive cell. The alphavirus replicon RNA vector (or replicon nucleic acid) can be derived from VEE, Sindbis virus, particularly TR339, South African Arbovirus No. 86, Semliki Forest virus, among others. Where a replicon nucleic acid is used, packaging functions are present in the cell in which the particles are produced, either from nucleic acid(s) introduced into the cell in trans or already present in the cell. For some alphavirus replicon vectors with certain heterologous coding sequences, the present inventors have observed that increasing the ratio of alphavirus glycoprotein helper nucleic acid improves packaging and/or ARP yield.

Advantageously, the cell in which the ARPs are produced is a cultured mammalian cell; but Vero cells, baby hamster kidney (BHK) cells, chicken embryo fibroblast (CEF) cells, DF-1, 293, 293T, Chinese Hamster Ovary (CHO) cells, and cultured insect cells are especially useful. Suitable available cultured insect cells include, without limitation, SF21, *Spodoptera frugiperda*; C6/36, *Aedes albopictus*; TRA-171, *Toxorhynchites amboinensis*; RML-12, *Aedes aegypti*; AP-61, *Aedes pseudoscutellaris*; and MOS-55, *Anopheles gambiae* cells.

Advantageously, the cells in which the ARPs are to be produced are synchronized in the G2/M phase of the cell cycle prior to electroporation with the alphavirus replicon vector and helper nucleic acid(s). Without wishing to be bound by any particular theory, it is believed that greater electroporation efficiency and transfer of nucleic acid to the nucleus (in those embodiments of the invention that involve nuclear activity) of the electroporated cell is achieved in such G2/M phase cells.

The alphavirus replicon nucleic acid can comprise a nucleotide sequence of interest to be expressed in the host cell. The nucleotide sequence can encode an immunogenic polypeptide, a cytokine or a therapeutic protein, among others, or the nucleotide sequence can be transcribed in the host cell to produce a functional RNA, such as a ribozyme, an interfering or an antisense molecule. If an alphavirus nucleic acid is used, it can be a wild-type virus, a recombinant virus which comprises a nucleotide sequence of interest as described above, or it can be an attenuated virus useful for producing an immunogenic response in the host.

Where the viral replicon nucleic acid and/or helper nucleic acid(s) are introduced by electroporation, it is especially effective to electroporate the cells where the cells are present at a concentration from about $10^7$ to about $10^9$ cells per mL, desirably from about $5\times10^7$ to about $1.5\times10^8$ per mL, electroporation medium, in the presence of sufficient replicon and help nucleic acid(s) to allow efficient packaging. The helper RNA molecule(s) need not be capped.

After the nucleic acid is introduced into the cells in which the ARPs will be produced, the cells are placed in culture vessels containing growth medium. For those cells that grow best as attached cells, the vessel comprises sufficient growth medium to allow growth, replicon RNA replication, packaging protein expression and viral replicon particle production, and sufficient surface area for those cells to attach and grow. The surface may be vessel, flask or plate walls, or hollow fibers, beads or other microcarriers of material appropriate for attached cell growth can be placed within the vessel. Vero cells or other cells grown on microcarriers (beads or discs) can be successfully electroporated on the carriers and cultured to produce ARPs at levels comparable to those achieved with unattached cells. Hollow fiber growth chambers or "cell cubes" are also useful. After the cells have grown and produced particles, typically from about 12 to about 48 hours, the particles are harvested. The cells can be separated from the growth medium, preferably pre-washed to remove cell debris and extraneous materials, and then washed with a small volume of Release Medium, with the result that the ARPs are freed from the cells and/or cell debris and can then be recovered in a purified, concentrated solution. The particles can be further purified using any of a number of techniques well known to the art, including but not limited to immunoaffinity chromatography, heparin affinity chromatography or ion exchange chromatography and the like.

BRIEF DESCRIPTION OF THE DRAWINGS

FIG. 1 shows the generation of ARPs using capped helper RNAs (left bar in each pair) and uncapped helper RNAs (right bar in each pair) in different types of cultured cells. Cells were electroporated with capped replicon RNA and capped or uncapped helper RNA molecules. ARPs were collected from the culture supernatants 24 hr post electroporation and titered on fresh Vero cells.

FIG. 2 shows the effect of post-electroporation growth medium on ARP yield. The results are given as the titer in the culture medium, the titer in the 1 M NaCl wash of the pelleted cells and the total titer (medium plus wash).

FIG. 3 shows the effects of growth medium pH on ARP yield. Vero cells were electroporated using a Petri dish electrode and inoculated into flasks with complete growth media adjusted to the specified pH values.

FIG. 4 shows the effect of different Cell Wash solutions used just prior to elution of the ARPs with the Release Medium; details are given in Example 7 herein below.

FIG. 5 shows the effect of using different salt compositions in the Release Medium on ARP yield. Concentrations and pH values of various Release Media are as shown.

FIG. 6 shows the yield of ARPs using a range of NaCl concentrations in the Release Medium.

DETAILED DESCRIPTION OF THE INVENTION

The following discussion and definitions are provided to improve the clarity of the present disclosure to one of ordinary skill in the relevant art.

In the context of the present application, nm means nanometer, mL means milliliter, VEE means Venezuelan Equine Encephalitis Virus, EMC means Encephalomyocarditis Virus, BHK means baby hamster kidney cells, HA means hemagglutinin gene, GFP means green fluorescent protein gene, N means nucleocapsid, FACS means fluorescence activated cell sorter, IRES means internal ribosome entry site, pfu means plaque forming units, iu means infectious units, and FBS means Fetal Bovine Serum. The expression "E2 amino acid (e.g., Lys, Thr, etc.) number" indicates designated amino acid at the designated residue of the E2 protein, and is also used to refer to amino acids at specific residues in the E3 or E1 proteins.

As used herein, the term "alphavirus" has its conventional meaning in the art, and includes the various species such as VEE Virus, Semliki Forest Virus (SFV), Sindbis, Ross River Virus, Western Equine Encephalitis Virus, Eastern Equine Encephalitis Virus, Chikungunya Virus, S.A. AR86, Everglades Virus, Mucambo Virus, Barmah Forest Virus, Middelburg Virus, Pixuna Virus, O'nyong-nyong Virus, Getah Virus, Sagiyama Virus, Bebaru Virus, Mayaro Virus, Una Virus, Aura Virus, Whataroa Virus, Banbanki Virus, Kyzylagach Virus, Highlands J Virus, Fort Morgan Virus, Ndumu Virus, and Buggy Creek Virus. The preferred alphaviruses used in the constructs and methods of the claimed invention are VEE, S.A. AR86, Sindbis (e.g. TR339, see U.S. Pat. No. 6,008,035), and SFV.

The terms "5' alphavirus replication recognition sequence" and "3' alphavirus replication recognition sequence" refer to the sequences found in alphaviruses, or sequences derived therefrom, that are recognized by the nonstructural alphavirus replicase proteins and lead to replication of viral RNA. These are sometimes referred to as the 5' and 3' ends, or alphavirus 5' and 3' sequences. In the constructs of this invention, the use of these 5' and 3' ends will result in replication of the RNA sequence encoded between the two ends. The 3' alphavirus replication recognition sequence as found in the alphavirus is typically approximately 300 nucleotides in length, which contains a more well defined, minimal 3' replication recognition sequence. The minimal 3' replication recognition sequence, conserved among alphaviruses, is a 19 nucleotide sequence (Hill et al., *J. Virology,* 2693–2704, 1997). These sequences can be modified by standard molecular biological techniques to further minimize the potential for recombination or to introduce cloning sites, with the proviso that they must be recognized by the alphavirus replication machinery.

The term "minimal 5' alphavirus replication recognition sequence" refers to the minimal sequence that allows recognition by the nonstructural proteins of the alphavirus but does not result in significant packaging/recombination of RNA molecules containing the sequence. In a preferred embodiment, the minimal 5' alphavirus replication recognition sequence results in a fifty to one-hundred fold decrease in the observed frequency of packaging/recombination of the RNA containing that sequence. Packaging/recombination of helpers can be assessed by several methods, e.g. the method described by Lu and Silver (*J. Virol. Methods* 2001, 91(1): 59–65).

The terms "alphavirus RNA replicon", "alphavirus replicon RNA", "alphavirus RNA vector replicon", and "vector replicon RNA" are used interchangeably to refer to an RNA molecule expressing nonstructural protein genes such that it can direct its own replication (amplification) and comprises, at a minimum, 5' and 3' alphavirus replication recognition sequences (which may be the minimal sequences, as defined above, but may alternatively be the entire regions from the alphavirus), coding sequences for alphavirus nonstructural proteins, and a polyadenylation tract. It may additionally contain a promoter or an IRES. It may also be engineered to express alphavirus structural proteins. Johnston et al. and Polo et al. (cited in the background) describe numerous constructs for such alphavirus RNA replicons, and such constructs are incorporated herein by reference. Specific embodiments of the alphavirus RNA replicons utilized in the claimed invention may contain one or more attenuating mutations, an attenuating mutation being a nucleotide deletion, addition, or substitution of one or more nucleotide(s), or a mutation that comprises rearrangement or chimeric construction which results in a loss of virulence in a live virus containing the mutation as compared to the appropriate wild-type alphavirus. Examples of an attenuating nucleotide substitution (resulting in an amino acid change in the replicon) include a mutation at nsP1 amino acid position 538, nsP2 amino acid position 96, or nsP2 amino acid position 372 in the alphavirus S.A.AR86, and an example of an attenuating mutation in the non-coding region of the replicon nucleic acid is the substitution of A or C at nucleotide 3 in VEE.

The terms "alphavirus structural protein/protein(s)" refers to one or a combination of the structural proteins encoded by alphaviruses. These are produced by the virus as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2. Attenuating mutations can be introduced into any one or more of the alphavirus structural proteins.

The term "helper(s)" refers to a nucleic acid molecule that is capable of expressing one or more alphavirus structural proteins.

The terms "helper cell" and "packaging cell" are used interchangeably herein and refer to the cell in which alphavirus replicon particles are produced. The helper cell comprises a set of helpers that encode one or more alphavirus structural proteins. As disclosed herein, the helpers may be RNA or DNA. The cell can be any cell that is alphavirus-permissive, i.e. cells that are capable of producing alphavirus particles upon introduction of a viral RNA transcript. Alphavirus-permissive cells include, but are not limited to, Vero, baby hamster kidney (BHK), 293, 293T, chicken embryo fibroblast (CEF), and Chinese hamster ovary (CHO) cells. In certain embodiments of the claimed invention, the helper or packaging cell may additionally include a heterologous RNA-dependent RNA polymerase and/or a sequence-specific protease.

The terms "alphavirus replicon particles", "virus replicon particles" or "recombinant alphavirus particles", used interchangeably herein, mean a virion-like structural complex incorporating an alphavirus replicon RNA that expresses one or more heterologous RNA sequences. Typically, the virion-like structural complex includes one or more alphavirus structural proteins embedded in a lipid envelope enclosing a nucleocapsid that in turn encloses the RNA. The lipid envelope is typically derived from the plasma membrane of the cell in which the particles are produced. Preferably, the alphavirus replicon RNA is surrounded by a nucleocapsid structure comprised of the alphavirus capsid protein, and the alphavirus glycoproteins are embedded in the cell-derived lipid envelope. The structural proteins and replicon RNA may be derived from the same or different alphaviruses. In a specific embodiment, the replicon RNA is derived from VEE and the structural proteins are derived from Sindbis Virus (see, e.g. Dubensky et al., U.S. Pat. No. 6,376,236). The alphavirus replicon particles are infectious but propagation-defective, i.e. the replicon RNA cannot propagate beyond the host cell into which the particles initially infect, in the absence of the helper nucleic acid(s) encoding the alphavirus structural proteins.

"Helper constructs", i.e. recombinant DNA molecules that express the alphavirus structural proteins, can be generated from a single helper that resolves itself into two separate molecules in vivo. Thus, the advantage of using a single helper in terms of ease of manufacturing and efficiency of production is preserved, while the advantages of a bipartite helper system are captured in the absence of employing a bipartite expression system. A DNA helper construct can be used, while in a second set an RNA helper vector is used. In the case of the DNA helper constructs that do not employ alphaviral recognition signals for replication and transcription, the theoretical frequency of recombination is lower than the bipartite RNA helper systems that employ such signals.

A promoter for directing transcription of RNA from DNA, i.e. a DNA dependent RNA polymerase, is employed to produce the alphavirus replicon and helper nucleic acids of the present invention. In the present context, a promoter is a sequence of nucleotides recognized by a polymerase and sufficient to cause transcription of an associated (downstream) sequence. In some embodiments of the claimed invention, the promoter is constitutive (see below). Alternatively, the promoter may be regulated, i.e., not constitutively acting to cause transcription of the associated sequence. If inducible, there are sequences present which mediate regulation of expression so that the associated sequence is transcribed only when (i) an inducer molecule is present in the medium in or on which the cells are cultivated, or (ii) conditions to which the cells are exposed are changed to be inducing conditions. In the present context, a transcription regulatory sequence includes a promoter sequence and can further include cis-active sequences for regulated expression of an associated sequence in response to environmental signals.

In the RNA helper embodiments and to produce the replicon RNA, the promoter is utilized to synthesize RNA in an in vitro transcription reaction, and specific promoters suitable for this use include the SP6, T7, and T3 RNA polymerase promoters. In the DNA helper embodiments, the promoter functions within a cell to direct transcription of RNA. Potential promoters for in vivo transcription of the construct include eukaryotic promoters such as RNA polymerase II promoters, RNA polymerase III promoters, or viral promoters such as MMTV and MoSV LTR, SV40 early region, RSV or CMV. Many other suitable mammalian and viral promoters for the present invention are available in the art. Alternatively, DNA dependent RNA polymerase promoters from bacteria or bacteriophage, e.g. SP6, T7, and T3, may be employed for use in vivo, with the matching RNA polymerase being provided to the cell, either via a separate plasmid, RNA vector, or viral vector. In a specific embodiment, the matching RNA polymerase can be stably transformed into a helper cell line under the control of an inducible promoter.

DNA constructs that function within a cell can function as autonomous plasmids transfected into the cell or they can be stably transformed into the genome. In these embodiments, the promoter may be a constitutive promoter, i.e. a promoter which, when introduced into a cell and operably linked to a downstream sequence, directs transcription of the downstream sequence upon introduction into the cell, without the need for the addition of inducer molecules or a change to inducing conditions. Alternatively, the promoter may be inducible, so that the cell will only produce the functional messenger RNA encoded by the construct when the cell is exposed to the appropriate stimulus (inducer). When using an inducible promoter, the helper constructs are introduced into the packaging cell concomitantly with, prior to, or after exposure to the inducer, and expression of the alphavirus structural proteins occurs when both the constructs and the inducer are present. Alternatively, constructs designed to function within a cell can be introduced into the cell via a viral vector, e.g. adenovirus, poxvirus, adeno-associated virus, SV40, retrovirus, nodavirus, picornavirus, vesicular stomatitis virus, and baculoviruses with mammalian pol II promoters.

Once an RNA transcript (mRNA) encoding the helper or RNA replicon vectors of this invention is present in the helper cell (either via in vitro or in vivo approaches, as described above), it is eventually translated to produce the encoded polypeptides or proteins. In certain embodiments, the RNA vector replicon is transcribed in vitro from a DNA plasmid and then introduced into the helper cell by electroporation. In other embodiments, the RNA vector replicon of this invention is transcribed in vivo from a DNA vector plasmid that is transfected into the helper cell (e.g. see U.S. Pat. No. 5,814,482), or it is delivered to the helper cell via a virus or virus-like particle.

The alphavirus RNA vector replicon is designed to express one or more heterologous coding sequence(s) or functional RNA(s) of interest, also referred to herein as a heterologous RNA or heterologous sequence, which can be chosen from a wide variety of sequences derived from viruses, prokaryotes or eukaryotes. Examples of categories of heterologous sequences include, but are not limited to, immunogens (including native, modified or synthetic antigenic proteins, peptides, epitopes or immunogenic fragments), cytokines, toxins, therapeutic proteins, enzymes, antisense sequences, and immune response modulators.

Any amino acids which occur in the amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

As used herein, expression directed by a particular sequence is the transcription of an associated downstream sequence. If appropriate and desired for the associated sequence, there the term expression also encompasses translation (protein synthesis) of the transcribed or introduced RNA. Alternatively, different sequences can be used to direct transcription and translation.

Alphavirus-permissive cells employed in the methods of the present invention are cells that, upon transfection with a complete viral RNA transcript, are capable of producing viral particles. Alphaviruses have a broad host range. Examples of suitable packaging cells include, but are not limited to, Vero cells, baby hamster kidney (BHK) cells, chicken embryo fibroblast cells, DF-1, 293, 293T, Chinese Hamster Ovary (CHO) cells, and insect cells.

The phrases "structural protein" or "alphavirus structural protein" as used herein refer to one or more of the alphaviral-encoded proteins which are required for packaging of the RNA replicon, and typically include the capsid protein, E1 glycoprotein, and E2 glycoprotein in the mature alphavirus (certain alphaviruses, such as Semliki Forest Virus, contain an additional protein, E3, in the mature coat). The term "alphavirus structural protein(s)" refers to one or a combination of the structural proteins encoded by alphaviruses. These are synthesized (from the viral genome) as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2.

As described herein, the structural proteins of the alphavirus are distributed among one or more helper nucleic acid molecules (e.g., a first helper RNA (or DNA) and a second helper RNA (or DNA)). In addition, one or more structural proteins may be located on the same molecule as the replicon nucleic acid, provided that at least one structural protein is deleted from the replicon RNA such that the replicon and resulting alphavirus particle are replication defective. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. The term "replication defective" as used herein is synonymous with "propagation-defective", and means that the particles produced in a given host cell cannot produce progeny particles in the host cell, due to the absence of the helper function, i.e. the alphavirus structural proteins required for packaging the replicon nucleic acid. However, the replicon nucleic acid is capable of replicating itself and being expressed within the host cell into which it has been introduced.

The helper cell, also referred to as a packaging cell, used to produce the infectious, replication defective alphavirus particles, must express or be capable of expressing alphavirus structural proteins sufficient to package the replicon nucleic acid. The structural proteins can be produced from a set of RNAs, typically two that are introduced into the helper cell concomitantly with or prior to introduction of the replicon vector. The first helper RNA includes RNA encoding at least one alphavirus structural protein but does not encode all alphavirus structural proteins. The first helper RNA may comprise RNA encoding the alphavirus E1 glycoprotein, but not encoding the alphavirus capsid protein and the alphavirus E2 glycoprotein. Alternatively, the first helper RNA may comprise RNA encoding the alphavirus E2 glycoprotein, but not encoding the alphavirus capsid protein and the alphavirus E1 glycoprotein. In a further embodiment, the first helper RNA may comprise RNA encoding the alphavirus E1 glycoprotein and the alphavirus E2 glycoprotein, but not the alphavirus capsid protein. In a fourth embodiment, the first helper RNA may comprise RNA encoding the alphavirus capsid, but none of the alphavirus glycoproteins. In a fifth embodiment, the first helper RNA may comprise RNA encoding the capsid and one of the glycoproteins, i.e. either E1 or E2, but not both.

In combination with any one of these first helper RNAs, the second helper RNA encodes at least one alphavirus structural protein not encoded by the first helper RNA. For example, where the first helper RNA encodes only the alphavirus E1 glycoprotein, the second helper RNA may encode one or both of the alphavirus capsid protein and the alphavirus E2 glycoprotein. Where the first helper RNA encodes only the alphavirus capsid protein, the second helper RNA may include RNA encoding one or both of the alphavirus glycoproteins. Where the first helper RNA encodes only the alphavirus E2 glycoprotein, the second helper RNA may encode one or both of the alphavirus capsid protein and the alphavirus E1 glycoprotein. Where the first helper RNA encodes both the capsid and alphavirus E1 glycoprotein, the second helper RNA may include RNA encoding one or both of the alphavirus capsid protein and the alphavirus E2 glycoprotein.

In all of the helper nucleic acids, it is understood that these molecules further comprise sequences necessary for expression (encompassing translation and where appropriate, transcription or replication signals) of the encoded structural protein sequences in the helper cells. Such sequences can include, for example, promoters (either viral, prokaryotic or eukaryotic, inducible or constitutive) and 5' and 3' viral replicase recognition sequences. In the case of the helper nucleic acids expressing one or more glycoproteins, it is understood from the art that these sequences are advantageously expressed with a leader or signal sequence at the N-terminus of the structural protein coding region in the nucleic acid constructs. The leader or signal sequence can be derived from the alphavirus, for example E3 or 6k, or it can be a heterologous sequence such as a tissue plasminogen activator signal peptide or a synthetic sequence. Thus, as an example, a first helper nucleic acid may be an RNA molecule encoding capsid-E3-E1, and the second helper nucleic acid may be an RNA molecule encoding capsid-E3-E2. Alternatively, the first helper RNA can encode capsid alone, and the second helper RNA can encode E3-E2-6k-E1. Additionally, the packaging signal or "encapsidation sequence" that is present in the viral genome is not present in all of the helper nucleic acids. Preferably, the packaging signal is deleted from all of the helper nucleic acids.

These RNA helpers can be introduced into the cells in a number of ways. They can be expressed from one or more expression cassettes that have been stably transformed into the cells, thereby establishing packaging cell lines (see, for example, U.S. Pat. No. 6,242,259). Alternatively, the RNAs can be introduced as RNA or DNA molecules that can be expressed in the helper cell without integrating into the cell genome. Methods of introduction include electroporation, viral vectors (e.g. SV40, adenovirus, nodavirus, astrovirus), and lipid-mediated transfection.

An alternative to multiple helper RNAs is the use of a single DNA molecule, which encodes all the polypeptides necessary for packaging the viral replicon RNA into infective alphavirus replicon particles. The single DNA helper can be introduced into the packaging cell by any means known to the art, including but not limited to electroporation, lipid-mediated transfection (lipofection), viral vectored (e.g. adenovirus or SV40), or calcium phosphate-mediated transfection. Preferably, the DNA is introduced via the electroporation-based methods of this invention. The DNA is typically electroporated into cells with a decrease in voltage and an increase in capacitance, as compared to that required for the uptake of RNA. In all electroporations, the value for the voltage and capacitance must be set so as to avoid destroying the ability of the packaging (host) cells to produce infective alphavirus particles. Alternatively, the helper function, in this format and under an inducible promoter, can be incorporated into the packaging cell genome prior to the introduction/expression of the RNA vector replicon, and then induced with the appropriate stimulus just prior to, concomitant with, or after the introduction of the RNA vector replicon.

Advantageously, one or more of the nucleic acids encoding the alphavirus structural proteins, i.e., the capsid, E1 glycoprotein and E2 glycoprotein, or the replicon construct, contains one or more attenuating mutations. The phrases "attenuating mutation" and "attenuating amino acid," as used herein, mean a nucleotide mutation (which may or may not be in a region of the viral genome encoding polypeptides) or an amino acid coded for by a nucleotide mutation, which in the context of a live virus, result in a decreased probability of the alphavirus causing disease in its host (i.e., a loss of virulence), in accordance with standard terminology in the art, See, e.g., B. Davis, et al., *Microbiology* 156–158, (4th ed. 1990), whether the mutation be a substitution mutation, or an in-frame deletion or addition mutation. The phrase "attenuating mutation" excludes mutations which would be lethal to the virus, unless such a mutation is used in combination with a "restoring" mutation which renders the virus viable, albeit attenuated. Methods for identifying suitable attenuating mutations in the alphavirus genome are known in the art. Olmsted et al. (1984; Science 225:424) describes a method of identifying attenuating mutations in Sindbis virus by selecting for rapid growth in cell culture. Johnston and Smith (1988; Virology 162:437) describe the identification of attenuating mutations in VEE by applying direct selective pressure for accelerated penetration of BHK cells. Attenuating mutations in alphaviruses have been described in the art, e.g. White et al. 2001 *J. Virology* 75:3706; Kinney et al. 1989 *Virology* 70:19; Heise et al. 2000 *J. Virology* 74:4207; Bernard et al 2000 *Virology* 276:93; Smith et al 2001 *J. Virology* 75:11196; Heidner and Johnston 1994 *J. Virology* 68:8064; Klimstra et al. 1999 *J. Virology* 73:10387; Glasgow et al. 1991 *Virology* 185:741; Polo and Johnston 1990 *J. Virology* 64:4438; and Smerdou and Liljestrom 1999 *J. Virology* 73:1092.

In certain embodiments, the replicon RNA comprises at least one attenuating mutation. In other specific embodiments, the helper nucleic acid(s) include at least one attenuating mutation. In embodiments comprising two helper nucleic acid molecules, at least one molecule includes at least one attenuating mutation, or both can encode at least one attenuating mutation. Alternatively, the helper nucleic acid, or at least one of the first or second helper nucleic acids includes at least two, or multiple, attenuating mutations. Appropriate attenuating mutations depend upon the alphavirus used. For example, when the alphavirus is VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threonine as E1 amino acid 253. Additional attenuating mutations include deletions or substitution mutations in the cleavage domain between E3 and E2 such that the E3/E2 polyprotein is not cleaved; this mutation in combination with the mutation at E1-253 is a preferred attenuated strain for use in this invention. Similarly, mutations present in existing live vaccine strains, e.g. strain TC83 (see Kinney et al., 1989, *Virology* 170: 19–30, particularly the mutation at nucleotide 3), are also advantageously employed in the particles purified by the methods of this invention.

Where the alphavirus is the South African Arbovirus No. 86 (S.A. AR86), suitable attenuating mutations may be selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid position 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372. Suitable attenuating mutations useful in embodiments wherein other alphaviruses are employed are known to those skilled in the art.

Attenuating mutations may be introduced into the RNA by performing site-directed mutagenesis on the cDNA which encodes the RNA, in accordance with known procedures. See, Kunkel, *Proc. Natl. Acad. Sci. USA* 82:488 (1985), the disclosure of which is incorporated herein by reference in its entirety. Alternatively, mutations may be introduced into the RNA by replacement of homologous restriction fragments in the cDNA which codes for the RNA, in accordance with known procedures, or in cDNA copies using mutagenic polymerase chain reaction methods.

The present invention provides improved methods for the preparation of infective, propagation-defective, highly immunogenic alphavirus replicon particles in high yields. In alphavirus replicon particles (ARPs), an alphavirus vector, herein referred to as a replicon, is engineered to contain and express one or more genes of interest, where the gene of interest can encode, for example, an antigen, a chemokine, a cytokine, a ribozyme, or an enzyme. The alphavirus replicon vector can be derived from any alphavirus, such as Venezuelan Equine Encephalitis (VEE) virus, Sindbis virus, e.g. strain TR339, South African Arbovirus No. 86, and Semliki Forest virus, among others. The vector is then introduced into cells in culture that allow replication of alphaviruses and in which the structural proteins of the alphavirus are also expressed, so that the vector is packaged by the structural proteins into ARPs which are eventually released from the cell. The present invention is also applicable to the preparation and harvesting of live, attenuated alphavirus particles, including particles as described in U.S. Pat. No. 5,643,576, and attenuated alphavirus strains used as vaccines against the alphavirus.

Because the traditional methods of producing and harvesting ARP are expensive, inefficient, and labor intensive, the present inventors examined various parameters to achieve improved ARP yield while simplifying the process and decreasing the cost per ARP. The novel process involves innovations at the steps of nucleic acid preparation, cell culturing, cell manipulation to produce the ARPs, ARP harvesting, and ARP formulation, and this process has the benefit of increasing yields of ARPs and reducing the cost per ARP significantly.

In all previous reports, ARPs were purified from the medium, or culture supernatant, in which the cells that produce the ARPs were grown. Surprisingly, when the present inventors washed ARP-producing cells with an aqueous solution containing a salt at a concentration higher than typically employed in normal growth medium, a significant number of infectious ARPs were released from the cells and/or cell debris. The immunogenicity of the ARPs collected after the salt wash step was compared to that of ARPs made according to known methods, and the strength of response to the ARPs collected with the salt wash were as good as or better than that for the ARP particles initially released into the medium before the salt wash.

In many applications, the use of the salt wash process to collect ARPs, as described herein, may obviate the need to collect ARPs from the cell culture medium, due to the large number of particles retained by the cells prior to the salt wash. The ratio of ARPs present in the medium prior to a salt wash to the ARPs retained by the cells and released with a salt wash can be from 1:1 to 1:400, depending on cell types, cell growth conditions, and salt wash conditions. In Vero cells, the ratio is typically at least 1:3, more commonly 1:10, 1:100 or 1:400 (see FIG. 4), depending on the degree of optimization of the other parameters of the claimed invention.

Therefore, disclosed herein are method(s) for preparing ARPs comprising the steps of (a) introducing an alphaviral replicon nucleic acid into a host cell, said replicon nucleic acid containing at least an alphavirus packaging signal and at least one coding sequence for a gene(s) of interest expressible in said alphaviral replicon nucleic acid, wherein the host cell is also capable of expressing alphavirus structural proteins required to produce ARPs, to produce a modified host cell; (b) culturing said modified host cell in a medium under conditions allowing expression of the structural proteins and replication of the alphaviral replicon nucleic acid, and then packaging of the alphaviral replicon nucleic acid to form ARPs; (c) separating the modified host cells from the medium, and (d) contacting the modified host cells after step (c) with a buffered solution having an ionic strength of at least approximately 0.20 M (herein the "Release Medium") to release the ARPs and produce an ARP-containing solution.

Step (d) may be performed with any one of a number of different Release Media, and the ARP "salt-wash" yield (i.e. the ARPs collected in the Release Medium) will be in part a function of the length of time the cells are exposed to the Release Medium. This period of time may be from 1 minute to several hours; 5 to 20 minutes is typical. In a preferred embodiment, a 0.5 M salt solution is used and the cells are incubated in this solution for approximately 5 minutes. The optimal combination of salt concentration in the Release Medium and the time of incubation can be determined straightforwardly by one of skill in the art, and will be additionally a function of the cell type and the cell support device.

The surprising observation that many of the ARPs are retained by the cells provides the opportunity to wash the cells thoroughly prior to the release of ARPs from the cells into a salt-containing solution, thus significantly reducing the need for downstream purification of the ARPs. The cell monolayers are thus effectively used as an affinity matrix for the ARPs.

Thus, in a preferred embodiment, the cells are cultured as described in step (b) above, in a receptacle, such as a cell culture flask, a roller bottle, a Cell-cube device, culture vessel (including bioreactor and spinner flask) with beads for attached cell growth, or a hollow-fiber device, where the cells are allowed to incubate from approximately 12 to 48 hours, preferably 16–24 hours, to generate ARPs. In the case where mammalian cells are utilized, the cells typically attach to the inner surfaces of the receptacle or to other solid support, including but not limited to beads, polystyrene particles, hollow fibers and the like, and after the requisite incubation period, the culture medium is desirably removed (decanted, aspirated, or the like) from the cells and is either reserved or discarded, thereby separating the modified host cells from the cell culture medium. Alternatively, cells growing in suspension culture can be centrifuged to remove the cells from the growth medium. The cells can then be washed extensively in a "Cell Wash" solution, which is a low- or no-salt containing medium that optionally contains additional components to help remove extraneous materials, e.g. a DNase preparation or other chemicals that remove residual cellular DNA or proteinases. A commercially available DNase is Benzonase, a *Serratia marcescens* deoxyribonuclease available from Novagen/EMD Biosciences, Madison, Wis. (see also U.S. Pat. No. 5,173,418). It can be incorporated in the post-electroporation medium at a concentration from about 10 to about 1000 units/mL. When the DNase, e.g., Benzonase, is incorporated in the ARP preparation, it is used at a concentration of 100 to 5000 units per mL, desirably about 500 units per mL, with incubation at 30 to 37° C. for 10 to 90 minutes, desirably about 30 minutes. Examples of useful Release Media (cell wash solutions for the release of bound ARPs) are presented in FIG. 4. These results indicate that the Cell Wash solution can be optimized for each cell-alphavirus strain combination to maximize retention of the ARPs (or alphavirus particles) by the cell substrate and minimize their release into the medium before addition of the Release Medium. By maximizing ARP retention by the cells, it may not be efficient or economical to harvest the much smaller number of particles present in the cell culture media.

After this extensive washing, the cells are then exposed to the Release Medium, and the ARPs are released into this medium from the host cells. In preferred embodiments, the Release Medium is an aqueous solution containing at least approximately 0.20 M salt, preferably between 0.25 M and 5 M salt, and it is typically a much smaller volume that the volume of medium in which the cells were grown, e.g. a 10- to 50-fold reduction in volume. It may contain additional components, such as DNAse, (particularly if it was not used in the Cell Wash solution) and stabilizers, e.g. HSA and sucrose. The temperature of the release step is not critical, similar results have been obtained at 4° C., room temperature and 37° C. Similar results are obtained with salt washes (in Release Medium) from 10 to 30 min.

The Release Medium can be made to the desired ionic strength with salts including, but not limited to, NaCl, KCl, $MgCl_2$, $CaCl_2$, $NH_4Cl$, $NH_4$ sulfate, $NH_4$ acetate and $NH_4$ bicarbonate. Desirably, the pH of the Release Medium is compatible with maintaining cell integrity, e.g. from about 6 to about 9.0, or from about 6.5 to about 8.5. In specific embodiments, the use of volatile salts in the Release Medium, such as the volatile ammonium salts, especially ammonium acetate or bicarbonate, allow the resulting ARP-containing solution to be lyophilized, with the result of removing the salt from the concentrated ARP preparation.

Several salts were tested for their abilities to facilitate harvest and recovery of ARPs from Vero cells at 16 and 24 hours post-electroporation. 1 M NaCl at pH 7.2, 1 M ammonium acetate at pH 7.35, 1 M ammonium bicarbonate at pH 7.4, 1 M magnesium chloride at pH 7.2, 1 M sodium acetate at pH 7.35 and 1 M ammonium sulfate at pH 7.35 all gave equivalent and good results. Increasing the salt concentration in the Release Medium from 0.5 M to 5 M did not affect yield of ARPs. Using a concentration toward the lower effective amount did prevent the need for large diluted volumes of material to be loaded onto chromatography media. 20 mM sodium phosphate at pH 7.2, 20 mM sodium phosphate at pH 6.5, 50 mM sodium phosphate at pH 7.2, and 20 mM sodium phosphate at pH 7.2 with 0.1% Tween 80 did not serve to effectively release ARPs from producing cells. Washes in Release Medium were carried out at 4° C., room temperature and 37° C.; wash temperature did not affect yield.

The effect of the medium into which the cells are placed immediately after electroporation, i.e. the post-electroporation medium, was also studied. See Example 3. Surprisingly good yields were obtained using serum-free medium, often equivalent to serum-containing medium, thus offering advantages with respect to potential safety of the products used and also in reducing the amount of protein potentially associated with the alphavirus-permissive cells and the virus particles or virus-like particles.

In a specific embodiment, the culture medium separated from the cells at step (c), as described above, can be combined with the ARP-containing solution described hereinabove, and ARPs can be purified at once from these two previously separate fractions. Alternatively, ARPs can be purified separately from the culture medium and then combined with the particles removed by salt washing.

In general, all steps of the claimed invention, including the growth of the cells prior to ARP production, can be performed in serum-free medium.

Although many methods are known for the introduction of nucleic acid molecules into host cells, a particularly useful method is electroporation. The present inventors determined that improved ARP yields were obtained when both cells and input nucleic acids in electroporation mixtures were present at concentrations higher than previously recommended or used.

Generally, the function of electroporation is to use an electric field to create pores or openings in the cell membranes sufficient to allow entry of the nucleic acids. Many devices are currently available commercially in which to electroporate cells, including disposable cuvettes (typically holding between 0.8 and 4 mL of medium), petri-dish electrodes, and flow-through apparati or other electroporation chambers. There is extensive teaching in the art on optimizing these devices for the electroporation of cells to effect genetic transformation, varying parameters such as the voltage, pulse duration, device geometry, the required field strength (which is a function of each cell type and depends on the cell radius and its critical breakdown voltage), and the distance between the electrodes. Additionally, the density of the cells is also a factor, and manufacturers' recommendations are between $1–5 \times 10^6$ cells/mL for Vero and NIH-3T3 cells, and slightly higher for BHK and CHO cells, both of which are smaller than Vero cells (see, e.g. Multiporator® Cuvette Manual, Brinkmann, Westbury, N.Y.; Genetronics, San Diego, Calif. (BTX Division) protocols for the Electro-Cell Manipulator (ECM®) or the ElectroSquarePorator™; Parham, J. et al. 1999 CytoTechnology 28:1–9). The art teaches that higher cell densities than those recommended result in non-homogenous field conditions in the electroporation milieu, which can lead to cell fusion. Liljestrom and Garoff, J. Virology 65:4107–4113, 1991, used electroporation to introduce a single, capped RNA helper and a Semliki Forest Virus replicon RNA into BHK cells at a concentration of $5 \times 10^6$ cells/mL.

Similarly, the concentration of nucleic acids used in the art has been empirically determined and is generally recommended to be between 5–20 μg DNA per mL of electroporation buffer; with larger amounts only considered effective for large nucleic acids. Liljestrom and Garoff (1991) studied the effect of RNA concentration in electroporation and reported that uptake efficiency was not linearly dependent on RNA concentration and that 2 μg was sufficient to obtain 100% transfection efficiency in a cuvette electroporation.

In the present invention, improved results (ARP yield per host cell) are obtained when the electroporation is carried out using host cells at a cell density of from about $1 \times 10^7$ to about $1 \times 10^9$ per mL electroporation medium. More preferably, the cell density in the electroporation milieu is from approximately $5 \times 10^7$ to $5 \times 10^8$ cells per mL. As specifically exemplified herein, the electroporation is carried out in an electroporation cuvette, but a Petri-dish or flow-through electroporation device, both of which are commercially available, can also be used. Other types of electroporation chambers can be used. Improved results were obtained with Vero cell concentrations from about $1 \times 10^7$ to about $5 \times 10^8$ per mL. For example, with $10^8$ cells in a 0.4 cm gap cuvette, $10^{10}$ to $10^{11}$ ARPs have been obtained from a single electroporation event. Equivalent yields on a cell and volume basis can be obtained by appropriately scaling the parameters in other electroporation devices. Alternatively, CHO, BHK, CEF, 293T and chicken embryo fibroblast cells can be used. Cultured insect cells, as discussed hereinabove, can also be used.

With an optimized cell concentration range for replicon-helper electroporation, each input helper RNA is present at about 10 to 50, desirably about 35 micrograms per mL (μg/mL), and the replicon RNA is present at about 10 to 150 μg/mL, desirably about 35 μg/mL. In other embodiments, one or more DNA helpers are used. The concentration of DNA helper(s) used in electroporation is typically higher than that used for RNA helpers, e.g. between 100 and 200 μg/mL. Using either RNA or DNA helpers, the amount of the alphavirus RNA replicon added to the cells prior to electroporation is approximately at least 35 μg/mL.

Thus, disclosed herein is a method for preparing ARPs comprising introducing an alphavirus replicon vector into an alphavirus-permissible cell culture via electroporation, wherein the concentration of the cells in the culture medium during electroporation is at least $10^7$ cells/mL medium, preferably between $5 \times 10^7$ and $5 \times 10^8$ cells/mL medium. While the preferred methods of the claimed invention involve the use of a replicon RNA which is then introduced into the cell, an alternative approach is to introduce the replicon RNA via a cDNA molecule encoding the replicon RNA. This approach is sometimes referred to as an eukaryotic layered vector initiation system (ELVIS), as described in U.S. Pat. Nos. 5,814,482 and 6,015,686.

Alphavirus structural proteins produced in the host cell can be encoded by one or more nucleic acid sequence(s) stably integrated within the genome of said host cell, or it/they can be introduced to the host cell in a transient form, either simultaneously with or prior to the introduction of the alphaviral replicon nucleic acid. Desirably, the alphavirus structural proteins provided in the host cell are expressed from one or two nucleic acid molecules (either RNA or DNA), which encode an alphavirus capsid protein capable of binding an alphaviral replicon nucleic acid, and at least one alphaviral glycoprotein, wherein said alphaviral glycoprotein associates with the alphaviral replicon nucleic acid and the capsid protein. When added as nucleic acids via electroporation, the one or more helper nucleic acids can be co-electroporated with the replicon RNA. In practicing the method of this invention with a single helper nucleic acid, a useful range for the molar ratio of replicon RNA:helper nucleic acid is between 1:2 and 1:8, and a useful range for the molar ratio of replicon RNA: first helper: second helper is between 1:2:2 and 1:5:5. Generally, the concentration of each helper can be optimized by routine experimentation, and it is not necessary or expected that both helpers will be used in equimolar amounts, particularly if one helper is an RNA molecule and another helper is a DNA molecule. The amounts of helper molecule(s) can be increased, relative to the amount of replicon nucleic acid but independently of each other, in the case of two helpers, to determine the concentration of helper(s) that generate the highest concentration of ARPs. In a specific embodiment of a single DNA helper that is expressing all the alphavirus structural proteins (e.g. a helper expressing all the VEE structural proteins is approximately 8.7 kb in length), a useful molar ratio of replicon RNA:DNA helper is approximately 1:6. Similarly, 30 μg of VEE replicon vector encoding the HIV gag protein and 100–150 μg of DNA helper (CMV promoter) was electroporated into Vero cells for ARP production. The DNA was highly purified to remove toxic contaminants and concentrated to about 5 mg/mL prior to electroporation. Generally, it is preferable to concentrate the DNA to between 1 and 8 mg/mL, preferably between 5 and 8 mg/mL. The DNA helper is present in the electroporation mixture at from about 20–500, desirably from about 50 to about 300, for example about 150 μg per 0.8 mL electroporation mixture, desirably containing from about $5 \times 10^7$ to about $2 \times 10^8$ cells, for example, about $1.2 \times 10^8$ cells.

One aspect of the efficient process of the present invention, for those embodiments utilizing replicon and/or helper RNA, is to carry out transcription from the linearized DNA vector encoding the replicon and helper nucleic acids without purification of that DNA after its linearization by restriction enzyme digestion. A protocol was developed for restriction enzyme digestion and RNA transcription in the same RNA transcription buffer (coupled reaction). The yield of RNA, if calculated per weight of input DNA, was 2–3 fold higher in the coupled reaction as compared to the previous methods in which the DNA was purified after linearization and before RNA transcription.

Additional savings in cost, reagents and labor contributing to this invention comes from the discovery that uncapped helper RNA(s) can be used in the electroporation reaction. Example 1 describes the experiments which were carried out to determine the efficiency of uncapped RNA(s) for use in electroporation together with a replicon RNA (see also FIG. 1).

We examined whether a cap structure was required on helper RNAs for them to be replicated and to provide structural proteins with which to package replicon RNAs (Example 1). Although there should be no theoretical requirement to cap helper RNAs, existing data from the inventors' laboratories as well as other laboratories indicated that uncapped helpers did not work efficiently (if at all) when generating ARPs. Nonetheless, because of the expense associated with capping the helper RNAs and the potential to significantly increase RNA yield from transcription reactions if the cap analog were not used, studies on the use of uncapped helpers to generate ARPs were initiated. Vero cells were electroporated with replicon RNA together with either capped or uncapped helper RNAs. Surprisingly, ARPs of equivalent titer were generated with either capped or uncapped RNA helpers (FIG. 1), provided that the RNA helpers were sufficiently purified before electroporation. Generation of ARPs with uncapped helpers was then attempted in other cell types (CHO, 293T and DF-1 cells) to confirm that this result was not limited to Vero cells. Uncapped helper RNAs were used to generate ARPs in Vero, CHO, DF-1 and 293T cells. ARPs generated with uncapped RNA helpers were equivalent in titer to ARPs generated with capped RNA helpers in all cell types tested (FIG. 1). The ability to use uncapped helper RNA molecules allows for significant cost savings in terms of reagents and RNA yield. By contrast, yields were higher for capped replicon RNAs than for uncapped replicon RNAs. Caps can include G cap, C cap, A cap, methylated G (m$^7$G(5'ppp(5')pppG(5)A); unmethylated G(G(5'ppp(5')A); ARCA (anti-reverse cap analog, 3-O-Me-m$^7$G(5')pppG(5); capping reagents are well known to the art and commercially available, for example, from Promega, Madison, Wis. and Ambion, Austin, Tex. The cost of RNA production is decreased significantly because the cap-analog reagent is an expensive component of the process and because each transcription reaction yields more RNA.

In comparing results with purified and unpurified RNAs in electroporation, it was determined that at least partial RNA purification (using commercially available kits and methods including, but not limited to, size exclusion chromatography, silica column chromatography, or LiCl) was necessary for good ARP yields. Purification removes molecules such as EDTA, HEPES, and TRIS (common constituents in nucleic acid manipulation), which are known to cause detrimental effects on transfection efficiencies obtained from electroporation (see, e.g. Brinkmann Instruments instruction manual), as well as the components of the transcription buffer used to generate the RNAs (see Example 2). Nucleic acid preparations used in the electroporation are preferably at an $A_{260}/A_{280}$ ratio of about 1.7 to 1.9 and are suspended in distilled water prior to electroporation. RNA purification has the added advantage of accomplishing a concentration of the RNA solutions. With a smaller volume for the RNA solution that is to be added to the cells in the electroporation medium, more cells can be used in the electroporation. Without wishing to be bound by any particular theory, it is believed that removal of divalent Mg cation or the reduction in Mg divalent cation to a concentration less than 5 mM prior to electroporation improves the ultimate ARP yield.

A single DNA helper can be used to produce ARPs when electroporated together with the alphavirus replicon RNA carrying the sequence of interest. While square wave and exponential wave electroporations gave similar results, the greater the purity of the DNA helper, the better the ARP yield. It was found that a lower voltage (with a higher capacitance) was preferable to efficiently introduce the DNA molecules into the cells, as compared with introducing only RNA molecules.

After the ARPs have been collected from the cells by salt wash, and optionally collected from the cell free supernatant, the ARPs can be purified by one or more steps including, but not limited to, ion exchange chromatography and heparin affinity chromatography. Heparin chromatography appears to work with several of the attenuated mutant alphavirus structural proteins incorporated in the ARPS, but not for the VEE 3000 virus structural proteins.

A preferred alphavirus for use in the present invention is Venezuelan equine encephalitis (VEE) virus. Preferably, the VEE strain used in producing the ARPs contains at least one attenuating mutation. On representative class of such attenuating mutations were first designed as "rapid-penetration" mutants (Johnston and Smith, Virology 162: 437–443, 1988), many of which were later shown to carry mutations in the E2 glycoprotein that resulted in a net positive charge (Davis et al., Virology 183:20–31, 1991) and also conferred an enhanced ability to bind glycosaminoglycans, e.g. heparan sulfate (see also Klimstra, WB et al. J. Virol. 72: 7357–7366, 1998; Bernard et al., Virology 276: 93–103, 2000). Similar mutations are known in other alphaviruses, e.g. Sindbis (Olmsted et al., Virology 148:245, 1986; Davis et al., Proc. Natl. Acad. Sci. USA 83: 6771, 1986); a specifically exemplified heparin-binding, attenuated VEE mutant is strain 3014. The viruses, or ARPs derived therefrom, that carry mutations conferring glycosaminoglycan-binding ability are particularly well suited for purification using the salt wash step, and they can also be further purified using heparin affinity chromatography.

Helper cells, in the context of this invention, are cells which, when helper and replicon nucleic acids are present therein, produce alphavirus replicon particles. Cells in which helper functions are encoded on one or more stably integrated sequences, can also be used to package ARPs. The DNA or RNA can be introduced by any means known to the art which is appropriate for the particular type of cell, including without limitation, transformation, lipofection or electroporation. Alternatively, stably transformed cells in which the structural genes required for the packaging of replicon nucleic acid into viral particles are integrated within the genome can also be used to prepare ARPs using the methods disclosed herein.

It is recognized by those skilled in the art that the coding sequences may vary due to the degeneracy of the genetic code and codon usage. All synonymous sequences which code for the antigen or other polypeptide or protein of interest are included within the scope of this invention.

Additionally, it is recognized by those skilled in the art that allelic variations may occur in the coding sequences which do not significantly change activity of the amino acid sequences of the peptides which those sequences encode. All such equivalent DNA sequences are included within the scope of this invention and the definition of a promoter.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

Pharmaceutical formulations, such as vaccines or other immunogenic compositions, of the present invention comprise an immunogenic amount of the infectious, propagation defective alphavirus replicon particles or live, attenuated particles in combination with a pharmaceutically acceptable carrier. An "immunogenic amount" is an amount of the infectious alphavirus particles which is sufficient to evoke an immune response in the subject to which the pharmaceutical formulation is administered. An amount of from about $10^4$ to about $10^9$, especially $10^6$ to $10^8$, infectious units, or ARPs per dose is believed suitable, depending upon the age and species of the subject being treated. Exemplary pharmaceutically acceptable carriers include, but are not limited to, sterile pyrogen-free water and sterile pyrogen-free physiological saline solution. Subjects which may be administered immunogenic amounts of the infectious, replication defective alphavirus particles of the present invention include human and animal (e.g., dog, cat, cattle, horse, donkey, mouse, hamster, monkeys, guinea pigs, birds, eggs) subjects. Administration may be by any suitable means, such as intraperitoneal, intramuscular, intradermal, intranasal, intravaginal, intrarectal, subcutaneous or intravenous administration.

One or more immuno-potentiator molecules, such as chemokines and/or cytokines can be can be incorporated in the immunogenic compositions comprising the alphavirus replicon particles prepared as described herein. Alternatively, the immunogenic compositions can comprise alphavirus replicon particles which direct the expression or one or more chemokines and/or cytokines in the patient or animal to which the composition is administered. Exemplary chemokines and/or cytokines include, without limitation, interleukin-4, interleukin-12, gamma-interferon, granulocyte macrophage colony stimulating factor, and FLT-3 ligand. It is understood that the choice of cytokine and/or chemokine may vary according to the neoplasia, parasite or pathogen which is targeted for an immune response.

Immunogenic compositions comprising the ARPs (which direct the expression of the sequence(s) of interest when the compositions are administered to a human or animal) produced using the methods of the present invention may be formulated by any of the means known in the art. Such compositions, especially vaccines, are typically prepared as injectables, either as liquid solutions or suspensions. Solid forms suitable for solution in, or suspension in, liquid prior to injection may also be prepared. Lyophilized preparations are also suitable.

The active immunogenic ingredients (the ARPs) are often mixed with excipients or carriers which are pharmaceutically acceptable and compatible with the active ingredient. Suitable excipients include but are not limited to sterile water, saline, dextrose, glycerol, ethanol, or the like and combinations thereof, as well as stabilizers, e.g. HSA or other suitable proteins and reducing sugars In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic product of the ARP resulting from administration of the immunogen in vaccines which are also comprised of the various adjuvants. Such additional formulations and modes of administration as are known in the art may also be used.

The immunogenic (or otherwise biologically active) ARP-containing compositions are administered in a manner compatible with the dosage formulation, and in such amount as will be prophylactically and/or therapeutically effective. The quantity to be administered, which is generally in the range of about $10^4$ to about $10^9$ infectious units per mL in a dose, depends on the subject to be treated, the route by which the ARPs are administered, the immunogenicity of the expression product, the types of effector immune responses desired, and the degree of protection desired.

Precise amounts of the active ingredient required to be administered may depend on the judgment of the physician, veterinarian or other health practitioner and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., weekly or at 1 to 4 months for a second dose, and if needed, a subsequent dose(s) after several months/years.

All references cited in the present application are incorporated by reference herein to the extent that there is no inconsistency with the present disclosure.

The following examples are provided for illustrative purposes, and are not intended to limit the scope of the invention as claimed herein. Any variations in the exemplified articles and methods which occur to the skilled artisan are intended to fall within the scope of the present invention.

EXAMPLES

Example 1

RNA Parameters Affecting ARP Yield

A. Use of Uncapped Helper RNAs in Various Cell Types
  293 T Cells
293T Cells were grown in DMEM medium with 10% FBS. Electroporation was performed in a 0.4 cm gap cuvette with a BTX square wave electroporator (Model 830; Genetronics, Inc., San Diego, Calif.) using $4.8 \times 10^7$ cells in PBS and 30 µg each of the following three RNAs (purified using an RNeasy Midi Kit #75142, Qiagen Corp., Valencia, Calif.): VEE capsid helper, VEE glycoprotein helper, and VEE GFP replicon. The helper RNAs were prepared by in vitro transcription with ("capped") or without ("uncapped") the addition of capped-G nucleotide in the transcription reaction. In the reactions that included the cap analog, the concentration of the rGTP was reduced proportionally. Four pulses at 360 V with a 450 µsec pulse length were used. After electroporation, the cells were seeded into T-75 flasks containing 25 mL media. ARPs were harvested from the media and titered on Vero cells.
  CHO Cells
CHO cells were grown on F-12 medium with 10% FBS. Electroporation was performed on a BTX square wave electroporator using $1.2 \times 10^7$ cells in PBS and 30 µg each of the following three RNAs: VEE capsid helper, VEE glycoprotein helper, and VEE GFP replicon. Four pulses at 580 V with a 450 µsec pulse length were used. After electroporation, the cells were seeded into T-75 flasks containing 25 mL media. ARPs were harvested from the media and titered on Vero cells.
  DF-1 (Chick)
DF-1 cells were grown on DMEM medium with 10% FBS. Conditions were as described for CHO cells.
  Vero
Vero cells were grown in EMEM medium with 10% FBS. Conditions were as described for CHO cells.

The results are presented in FIG. 1, showing the IFU/mL obtained when using uncapped vs. capped helper RNAs in the indicated cell types.

B. Effect of RNA Purification and Capping on ARP Yield

In an experiment employing an HIV-gag encoding replicon vector RNA and two helper RNAs encoding the VEE capsid and glycoprotein genes, in vitro transcription reactions were performed using a commercially available kit from Promega Corporation (Madison, Wis.; Cat No. P1300). To prepared capped helper and replicon RNAs, capped-G was added to the transcription reaction, and the rGTP concentration was reduced by 1.4 mM as compared to the other rNTPs. To prepare uncapped helper RNA, the four rNTPs were used as equimolar concentrations. RNA purification was accomplished using the Promega SV total RNA Isolation System (Promega Corp., Madison, Wis.; Catalog No. Z3100, a silica resin) and eluting the RNA into RNAse-free water. Other methods of RNA purification are also suitable, such as size-exclusion chromatography, but a key parameter is to use a method that generate a very pure, concentrated RNA solution, i.e. at least 0.5 µg/uL, preferably at least 2–3 µg/µL. The concentrations of the purified RNAs were determined using a spectrophotometer, while the concentration of the unpurified RNAs (obtained by using the transcription reaction directly) was estimated by running a 1 µl aliquot in a formaldehyde gel with aliquots of known RNA quantities.

Equal amounts of each of the helper RNAs, either 5 or 30 µg, capped or uncapped, were electroporated into $1.2 \times 10^7$ VERO cells in a final volume of 800 µl using a 0.4 cm gap electroporation cuvette (4 pulses at 580V, 25 µF), along with 30 µg of the HIV-gag encoding replicon vector RNA. After electroporation, the cells were seeded into a T75 flask with 25 mL HyQMEM+10% FBS, and incubated overnight at 37° C. and 5% $CO_2$. ARPs were collected at 24 hours, filtered, and titered on VERO cells. The results are presented in Table 1.

TABLE 1

| | RNA Parameters | | |
|---|---|---|---|
| RNA Amount | RNA Purified? | RNA Capped? | ARP Yield |
| 5 µg | No | Yes | $3.84 \times 10^3$ |
| 5 µg | No | No | $4.27 \times 10^2$ |
| 5 µg | Yes | Yes | $2.77 \times 10^5$ |
| 5 µg | Yes | No | $4.27 \times 10^3$ |
| 30 µg | No | Yes | $2.56 \times 10^4$ |
| 30 µg | No | No | $1.07 \times 10^3$ |
| 30 µg | Yes | Yes | $2.13 \times 10^6$ |
| 30 µg | Yes | No | $2.56 \times 10^6$ |

Purification of the RNA (both helpers and vector replicon RNA) prior to electroporation into cells dramatically improves the yield of ARPs (compare Rows 1&2 to 3&4 and Rows 5&6 to 7&8). Furthermore, with the use of purified RNA, capping of the helper RNAs is not required at higher RNA concentrations (compare Row 1 to Row2, 3 to 4, 5 to 6, and 7 to 8).

Similar results were obtained using uncapped helper RNA(s) with an alphavirus replicon vector in which a sequence encoding PSMA (prostate cancer antigen) was inserted.

Example 2

Key Parameters in RNA Purification

Replicon and helper RNAs were prepared as described in Example 1. For electroporation, 30 µg each replicon and helper RNAs were combined in RNase-free microcentrifuge tubes. Control tubes had either purified or unpurified RNAs alone, while the remaining tubes additionally received 5× transcription reaction buffer [400 mM HEPES-KOH (pH 7.5); 120 mM MgCl$_2$; 10 mM spermidine; 200 mM DTT), Not I restriction enzyme, T7 enzyme mix (T7 RNA-dependent RNA polymerase, RNase inhibitor, pyrophosphatase), or combinations of these three. Final concentrations of each transcription reaction component were approximately equivalent to that in an equal volume of unpurified RNA. 1.2×10$^7$ VERO cells were added to each microcentrifuge tube, and the mixture was transferred to a 0.4 cm gap electroporation cuvette. Cells were pulsed 4 times at 580 V and 25 µF, and allowed to recover at room temperature for 10 min. Electroporated cells were seeded into T75 flasks containing 25 mL HyQMEM with 10% fetal bovine serum and antibiotics. Aliquots were seeded into 96 well plates for analysis of electroporation efficiencies.

VERO cells in 96 well plates were fixed with MeOH and analyzed for replicon or helper protein expression by immunofluorescence assay (IFA). Efficiencies from purified RNAs were greater then 90% for all three RNAs, while efficiencies from unpurified RNA controls was 50% or less. Addition of Not I or T7 enzyme mix alone to purified RNAs had little to no effect on electroporation efficiencies. The addition of transcription buffer alone or in combination with other transcription reaction components decreased electroporation efficiencies to 10% or less.

The culture medium was collected from T7 flasks and filtered to remove cellular debris. ARP yield from each electroporation were determined by titering on Vero cells in 96 well plates. As shown in Table 2, ARP yields using unpurified RNAs decreased by two logs compared to yields using purified RNAs. Not I or T7 enzyme mix had no significant effect on ARP yields when added to purified RNAs alone; however, addition of T7 transcription reaction buffer in any combination resulted in a 4 log or greater decrease in ARP yields compared to purified RNAs.

These results suggest that one or more components of the transcription reaction buffer can have a negative effect on electroporation efficiencies and ultimately on ARP yield. The significant decrease in ARP yields when T7 transcription buffer is added to purified RNA as compared to unpurified RNAs containing T7 transcription buffer suggests that the effect is quantitative, since the concentration of buffer components was higher in the purified RNA sample.

TABLE 2

Effect of RNA Manipulation on ARP Yield

| RNA | In Vitro Transcription Component | Yield of ARP |
|---|---|---|
| Purified | None | 1.4 × 10$^7$ |
| Unpurified | None | 1.1 × 10$^5$ |
| Purified | 1X Buffer | lod* |
| Purified | Not I enzyme | 1.9 × 10$^7$ |
| Purified | T7 enzyme mixture | 3.2 × 10$^6$ |
| Purified | 1X Buffer + Not I enzyme | lod |
| Purified | 1X Buffer + T7 enzyme mixture | lod |
| Purified | Not I enzyme + T7 enzyme mix | 1.4 × 10$^7$ |
| Purified | 1X Buffer, Not I, T7 enzyme mix | lod |

*lod = at or below the limit of detection (approx. 2.1 × 10$^3$ ARP/mL)

Example 3

Effect of Electroporation Conditions on ARP Yield

In initial experiments with the electroporation of certain cell lines for electroporation, for example with 293T and CEF cells, it was observed that higher ARP yields could be obtained by increasing the concentration of cells in the electroporation mixture, while maintaining the same amount of input nucleic acids.

A. Experiment 1

Vero cells were resuspended at the indicated concentration in PBS in a 0.4 cm gap cuvette, with 30 µg replicon RNA (encoding a cancer tumor antigen), 26.8 µg VEE capsid RNA helper, and 55.6 µg VEE glycoprotein RNA helper. Following electroporation, the cells were seeded into one or more flasks, as needed, at a density of 1.4×10$^5$ cells/cm$^2$ growth area with approximately 0.3 mL growth media per cm$^2$. Twenty-three hours post-electroporation, media was collected from each flask, and the cell monolayers were washed with approximately 10 mL serum-free media. This wash solution was added to the collected media from each flask. A salt-wash was then performed in each flask, using 0.5 M NaCl for 10 minutes. The salt wash was collected and analyzed separately. Where indicated, a second salt wash was performed and analyzed separately. ARP yields are presented in Table 3 as the total number of particles obtained from a single cuvette electroporation.

TABLE 3

Wash Parameters and ARP Yield

| Cell Concentration Cells/mL; relative unit | Volume of media or salt wash | ARP yield | Total ARP yield (salt wash + media) |
|---|---|---|---|
| 3 × 10$^7$ 2X | 50 mL media | 9.0 × 10$^7$ | |
| | 10 mL salt wash | 6.9 × 10$^8$ | 7.8 × 10$^8$ |
| 9 × 10$^7$ 6X | 150 mL media | 6.2 × 10$^8$ | |
| | 30 mL salt wash #1 | 1.1 × 10$^9$ | |
| | 30 mL salt wash #2 | 4.5 × 10$^8$ | 2.2 × 10$^9$ |
| 1.2 × 10$^8$ 8X | 225 mL media | 3.2 × 10$^8$ | |
| | 30 mL salt wash #1 | 2.4 × 10$^9$ | |
| | 30 mL salt wash #2 | 1.2 × 10$^9$ | 3.9 × 10$^9$ |
| 1.5 × 10$^8$ 10X | 300 mL media | 4.8 × 10$^8$ | |
| | 60 mL salt wash #1 | 3.8 × 10$^9$ | |
| | 60 mL salt wash #2 | 1.4 × 10$^9$ | 5.7 × 10$^9$ |

Thus, a five-fold increase in cell concentration, without any increase in the amount of RNA used in the electroporation, results in a nearly 10-fold increase in ARP yield.

B. Packaging ARPs With a Single DNA Helper

Vero cells were resuspended in InVitrus serum-free medium at the indicated cell densities. The cells were electroporated using 30 µg of a VEE HIV-gag replicon RNA and 100–150 µg VEE DNA helper expressing all the VEE structural proteins under an CMV promoter. The DNA helper was purified and concentrated to at least 5 mg/mL before use in electroporation.

After electroporation, the cells were incubated for 10 minutes at room temperature, and then they were transferred to 4 mL OptiPro, which was then split evenly into two T300 flasks each containing 100 mL OptiPro. The cells were incubated overnight at 37 C and 5% CO$_2$. The ARPs were harvested by first aspirating the media off the cells and passing it through a 0.2 micron filter into a sterile container. The cells in the flask were washed for 5 minutes at room temperature with 10 mL of a 1 M NaCl solution in 20 mM NaPi, pH 7.2–7.4. The salt wash was transferred to the used filter and incubated for 5 minutes at room temperature. This salt wash passed through the filter into a clean and separate container from the media. Media and salt wash were kept and titered separately. Total IFU, as reported in Table 4, represent the sum of the salt wash and media; generally, the media contained an insignificant number of ARPs as compared to the salt wash. Similar results were obtained using a salt wash solution of 0.5 M NaCl.

C. Experiment 3.

A Corning Cell Cube (Corning, Inc., Acton, Mass.) was used to grow a large quantity of cells. A single electroporation was performed using $5 \times 10^8$ Vero cells in a 1 cm gap electroporation cuvette. 150 µg each of a VEE replicon (encoding HIV-gag), VEE capsid helper, and VEE glycoprotein helper were electroporated into the cells using 4 pulses at 1150V, 25 uF on a Bio-Rad electroporator (Gene Pulser II, BioRad Laboratories, Inc., Hercules, Calif.; Catalog No. 165-2105). After electroporation, the cells were seeded into 5 T-300 flasks containing 100 mL OptiPro SFM (Invitrogen, Carlsbad, Calif.; Catalog No. 12309019). Twenty-four hours post-electroporation, media was collected from each flask and combined for titering. A salt-wash was then performed in each flask, using 20 mL of a 1.0 M NaCl in each flask, and the salt washes were combined for titering. The total yield of ARP in the media was $1 \times 10^8$ i.u.; the total yield of ARP in the salt wash was $2.2 \times 10^{11}$ i.u.

Example 4

Post-Electroporation Culture Parameters

A. Post-Electroporation Growth Medium

In the prior reports of ARP production, cells are seeded into medium containing 10% FBS post electroporation. To examine the effects of serum on ARP yield, cells were seeded in different media with varying concentrations of serum. An optimal post electroporation medium would not require the use of serum and would have a low protein concentration. Media with lowered serum contents as well as three serum-free media were examined for use in high cell density electroporations: OptiPro serum free medium, Gibco Cell Culture/Invitrogen, San Diego, Calif.; VP-SFM, VP Serum Free Medium, Gibco Cell Culture/Invitrogen, San Diego, Calif.; Ex-Cell 505, JRH Biosciences, Lenexa, Kans.; and InVitrus chemically defined cell culture medium, (Cell Culture Technologies GmbH, Zurich, CH; Catalog No.IVT). All of these media have a buffered pH between 7.0 and 7.4. Vero cells were electroporated with helper and replicon RNAs. The electroporation mixture was divided among 8 T-75 flasks containing the different media. The cells were cultured for 18–24 hours at 37° C. Analysis of the ARP yields revealed that serum levels in EMEM can be reduced from 10% to 1% with no significant decrease in ARP yields. Also, OptiPro medium gave ARP yields equivalent yields to those in EMEM+10% FBS. OptiPro, which is free of human and/or animal proteins, gave equivalent ARP yields to those obtained using EMEM+10% FBS for several different ARPs. Serum-free media useful for the post-electroporation growth and ARP production include several commercially available media:

B. The Effect of Post-Electroporation Growth Medium pH

Figure 4:
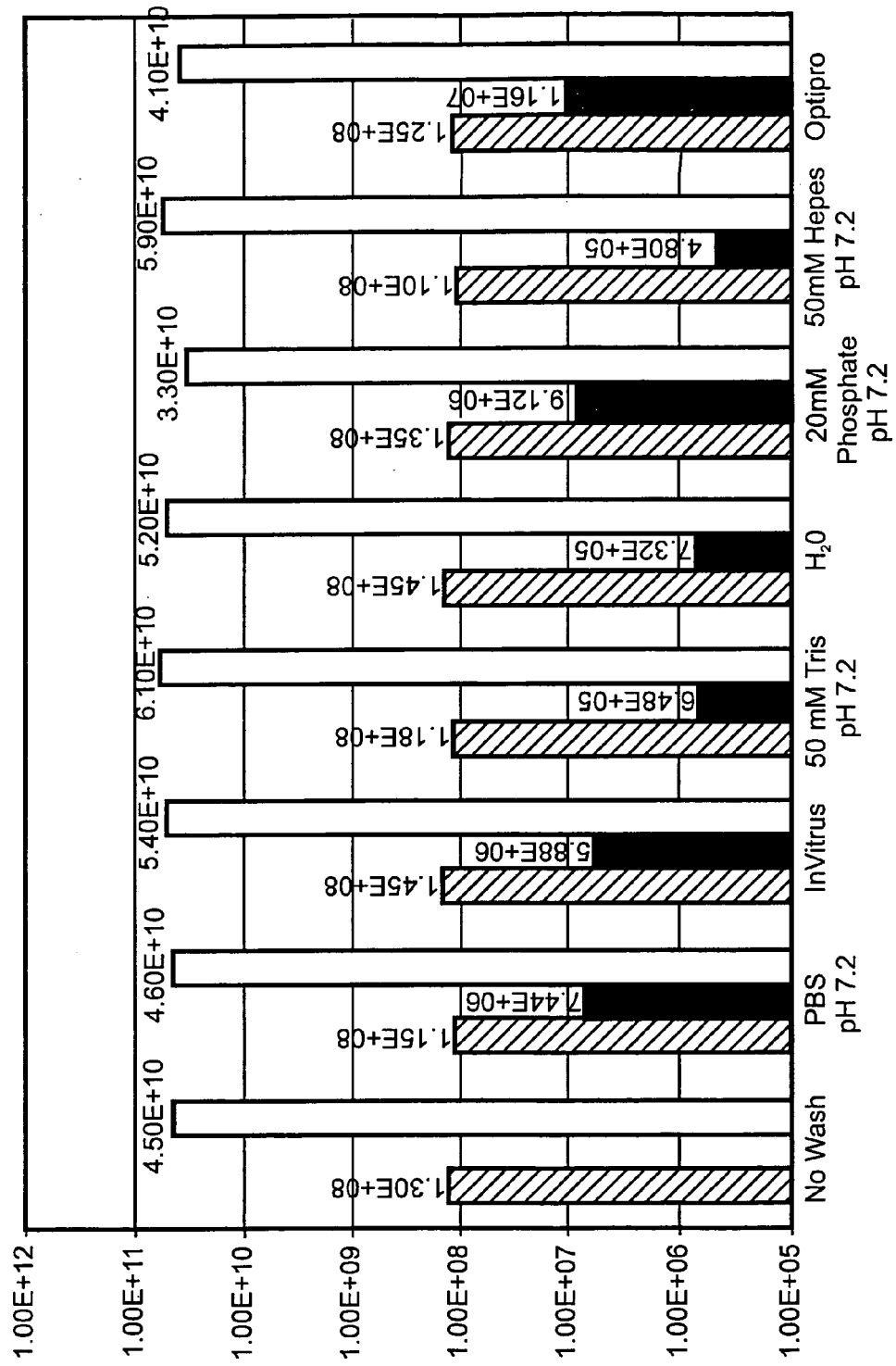

The effect of the pH of the post electroporation growth medium on ARP yield was also examined. Vero cells were electroporated in a Petri dish electrode apparatus, and aliquots were inoculated into complete growth medium adjusted to the pH of interest. The results are shown in FIG. 4.

C. Hollow Fiber Cartridges for Post-Electroporation Cell Growth

It has been discovered that electroporated cells adhere rapidly to polysulfone fibers, such as those in the FiberCell HF Cartridge (Fibercell Systems, Inc.; Frederick, Mo.; Catalog No: 4300-C2011). Placing the electroporated cells into a hollow fiber provides advantages for harvesting the ARPs produced by the cells in the hollow fibers. The final volume into which the ARPs can be eluted may be as little as 40 mL (using a small cartridge which can hold up to $10^9$ cells) to 100 mL (larger cartridge that can hold up to $5 \times 10^{10}$ cells).

TABLE 4

Cell Density and ARP Yield

| Vero Cell Density In Electroporation Cuvette (cells/mL) | ARP yield (Total IFU) |
| --- | --- |
| $2.5 \times 10^7$ | $6.5 \times 10^8$ |
| $5.0 \times 10^7$ | $9.5 \times 10^8$ |
| $7.5 \times 10^7$ | $3.6 \times 10^9$ |
| $1.0 \times 10^8$ | $3.45 \times 10^9$ |
| $1.3 \times 10^9$ | $6.4 \times 10^9$ |

Example 5

Effect of Helper RNA Concentration on ARP Yields

Electroporation in a 0.4 cm gap cuvette was performed using $1 \times 10^8$ Vero cells. Each electroporation included 30 µg each of the HIV-gag VEE replicon RNA and the VEE glycoprotein helper; the concentration of the VEE capsid helper was varied, as indicated. Electroporation was performed on a Bio-Rad instrument using the following conditions: 4 pulses at 580V, 25 uF (resulting pulse length: approx. 0.8 ms). The cells were seeded into 50 mL of either EMEM+FBS or OptiPro, as indicated, in T175 flasks. Twenty-four hours after electroporation, the medium from each flask was harvested and filtered. Five mL of 1 M NaCl was added to each flask and was allowed to incubate with the attached cells for 5 minutes. The salt wash solution was then removed and filtered through the same filter used for the previously collected medium.

TABLE 5

RNA Concentration, Medium and ARP Yield

|  | Media | Salt Wash |
| --- | --- | --- |
| 30 µg capsid RNA/EMEM + FBS | $2.20 \times 10^9$ | $9.70 \times 10^{10}$ |
| 30 µg capsid RNA/Optipro | $2.12 \times 10^9$ | $9.10 \times 10^{10}$ |
| 90 µg capsid RNA/Optipro | $3.12 \times 10^9$ | $7.70 \times 10^{10}$ |
| 80 µg capsid RNA/Optipro | $4.80 \times 10^8$ | $8.00 \times 10^{10}$ |
| 30 µg truncated capsid RNA/Optipro | $1.50 \times 10^9$ | $9.00 \times 10^{10}$ |
| 90 µg truncated capsid RNA/Optipro | $2.36 \times 10^9$ | $8.30 \times 10^{10}$ |

Example 6

DNA Helper and Electroporation Conditions

Typically, larger amounts of DNA and somewhat different electroporation conditions are needed to obtain efficient electroporation of DNA helpers into VERO cells, as compared to the amounts and conditions used for RNA helpers. For example, DNA helpers are electroporated using 250 V, 950 μF or 2–3 pulses (30 msec) at 250 V, 800 μF, while RNA helpers are electroporated using 580 V, 25 μF (four pulses).

As with the RNA, the DNA helper (or helpers) are desirably purified prior to electroporation. In a 0.4 cm gap electroporation cuvette, with $1 \times 10^8$ Vero cells and a single DNA helper encoding all the VEE structural proteins, electroporation was carried out using two different electroporation devices. The first machine provides an initial voltage pulse that decays exponentially. Using 100 or 150 μg DNA (from a purified solution at a concentration of at least 5 mg/mL), a useful set of conditions is a single pulse at 250V, 950 uF, which delivers a pulse of approximately 20 to 30 milliseconds. The capacitance can be reduced, e.g. to 800 uF, and 2–3 pulses at 250V provides approximately the same ARP yield. On a second machine that delivers the voltage in the form of a square wave, a pulse between 20 and 50 msec at 300V provided similar results as the first machine. This procedure can be optimized for all cell types by varying pulse length, shape, voltage, capacitance and number. Vero cells typically do not survive a 25 msec pulse above 400V. Since these conditions are harsher than those necessary to deliver the vector replicon RNA, particles prepared using a DNA helper are electroporated at the optimized conditions for DNA, and the vector replicon RNA enters the cells efficiently in these conditions.

$10^8$ cells in 0.8 mL were electroporated using 30 μg of a VEE HIV-gag replicon RNA and 150 μg VEE DNA helper expressing all the VEE structural proteins under the regulatory control of a CMV promoter. After electroporation, the cells were handled and ARPs collected and titered as described above, and the results are shown in the table below.

TABLE 6

Electroporation Conditions and ARP Yield

| Voltage (V) | Capacitance (μF) | # Pulses | Total IU |
|---|---|---|---|
| 250 | 950 | 1 | 5.2e6 |
| 300 | " | 1 | 3.9e6 |
| 350 | " | 1 | 2.9e6 |
| 400 | " | 1 | 0 |
| 450 | " | 1 | 0 |
| " | " | 1 | 0 |
| 250 | 800 | 2 | 5.2e6 |
| " | " | 3 | 4.3e6 |
| 350 | 650 | 2 | 0 |
| " | " | 3 | 1.4e6 |
| 250 | 950 | 2 | 4.7e6 |

It is noted that the experiment for which the data is presented above, the insufficient purity of the DNA helper preparation is believed responsible for the relatively low overall yields, but these data document the relative effects of electroporation parameters.

Example 7

Synchronization of Cells for ARP Production

The effect of synchronizing cells in the G2/M phase of the cell cycle on electroporation efficiency was examined. Cells were treated at 2 hrs post plant with 1 μg/mL aphidicolin in DMSO (Sigma Chemical Co., St. Louis Mo.) for 20 hr, allowed to rest for 4 hr and harvested for electroporation (Golzio et al. (2002) Biochem. Biophys. Acta 1563:23–28). Helper DNA electroporations (together with replicon RNA) were carried out as described herein. Cells were observed for growth and cell morphology throughout the treatment process. With each group of cells, a flask containing a DMSO treatment control was carried with the aphidicolin/DMSO treated flasks. There were no negative effects on the general health of the cells during treatment in the test or control flasks. It was determined that it was beneficial to obtain confluency within a two hr incubation prior to starting the synchronization protocol. The cell sheeting was best at 90–100% prior to the start of the aphidicolin treatment because further cell division was prevented by the treatment. Using Vero cells, it was found that a density of $4.0 \times 10^5$ cells/cm$^2$ was too high; a cell density of $1.1 \times 10^4$ cells/cm$^2$ resulted in 90% confluency in 2 hr.

Example 8

Pre-Wash Solutions and ARP Yields

After the ARPs have been produced by the electroporated cells, the cells can be washed extensively with a Cell Wash Solution to remove extraneous materials before harvesting of the ARPs begins. The choice of Cell Wash Solution affects the number of ARPs released during this pre-washing step.

A single electroporation was performed in a 0.4 cm gap cuvette using $1 \times 10^8$ Vero cells and 30 μg each VEE HIV-gag replicon RNA, VEE capsid helper RNA, and VEE glycoprotein helper RNA. The cells were seeded equally into 8 T-75 flasks, each containing 25 mL OptiPro media. After 24 hours, the media was removed, the cell monolayers were washed with 6 mL of the indicated Cell Wash solution, and the cells were finally washed with 6 mL of 1 M NaCl (phosphate buffered to pH 7.2). The media, Cell Wash, and salt-wash solutions were analyzed separately for ARP yield by titering on VERO cells. The results are presented in FIG. 4

Example 9

Salt Wash Parameters

A. Salt Composition

Figure 3:
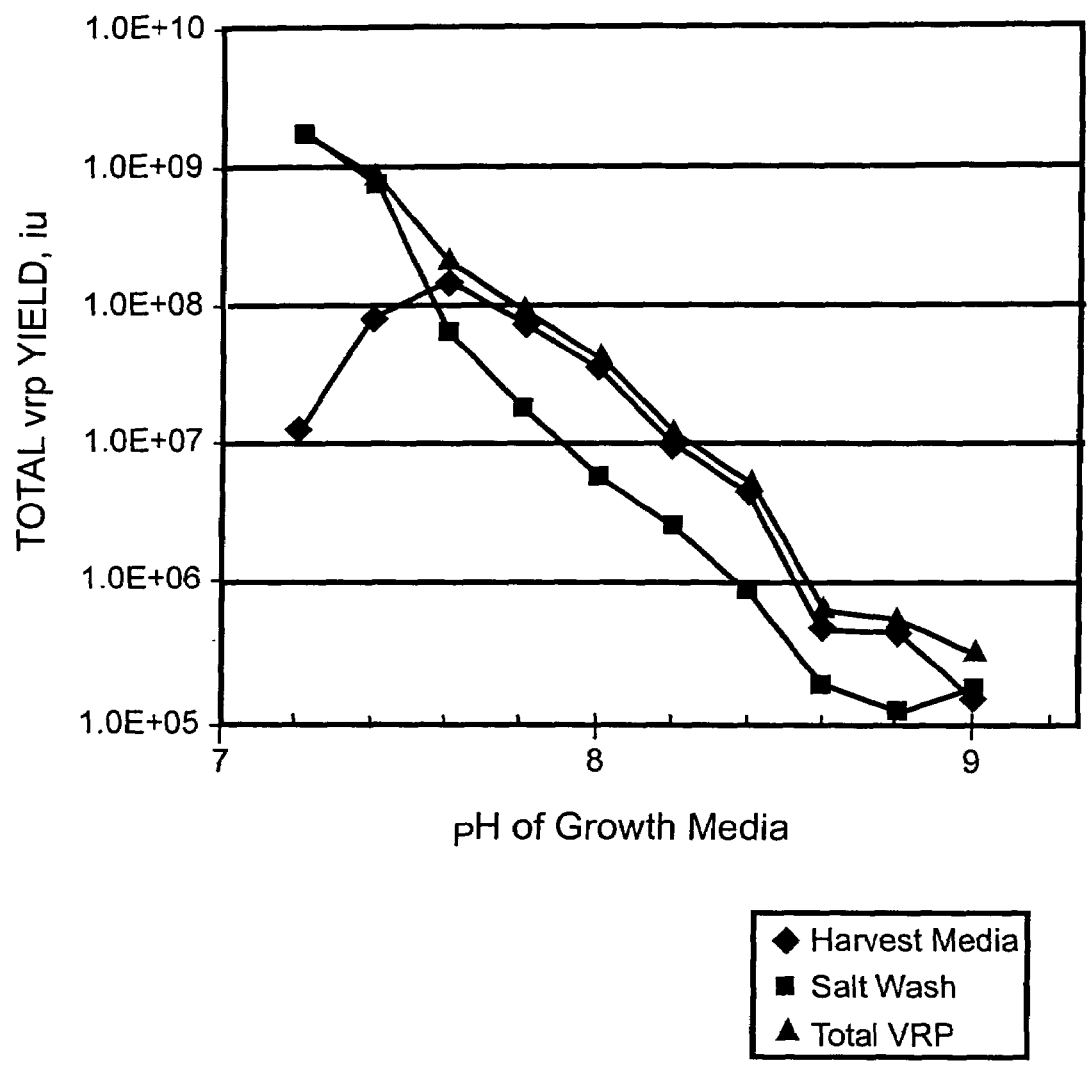
Figure 5:
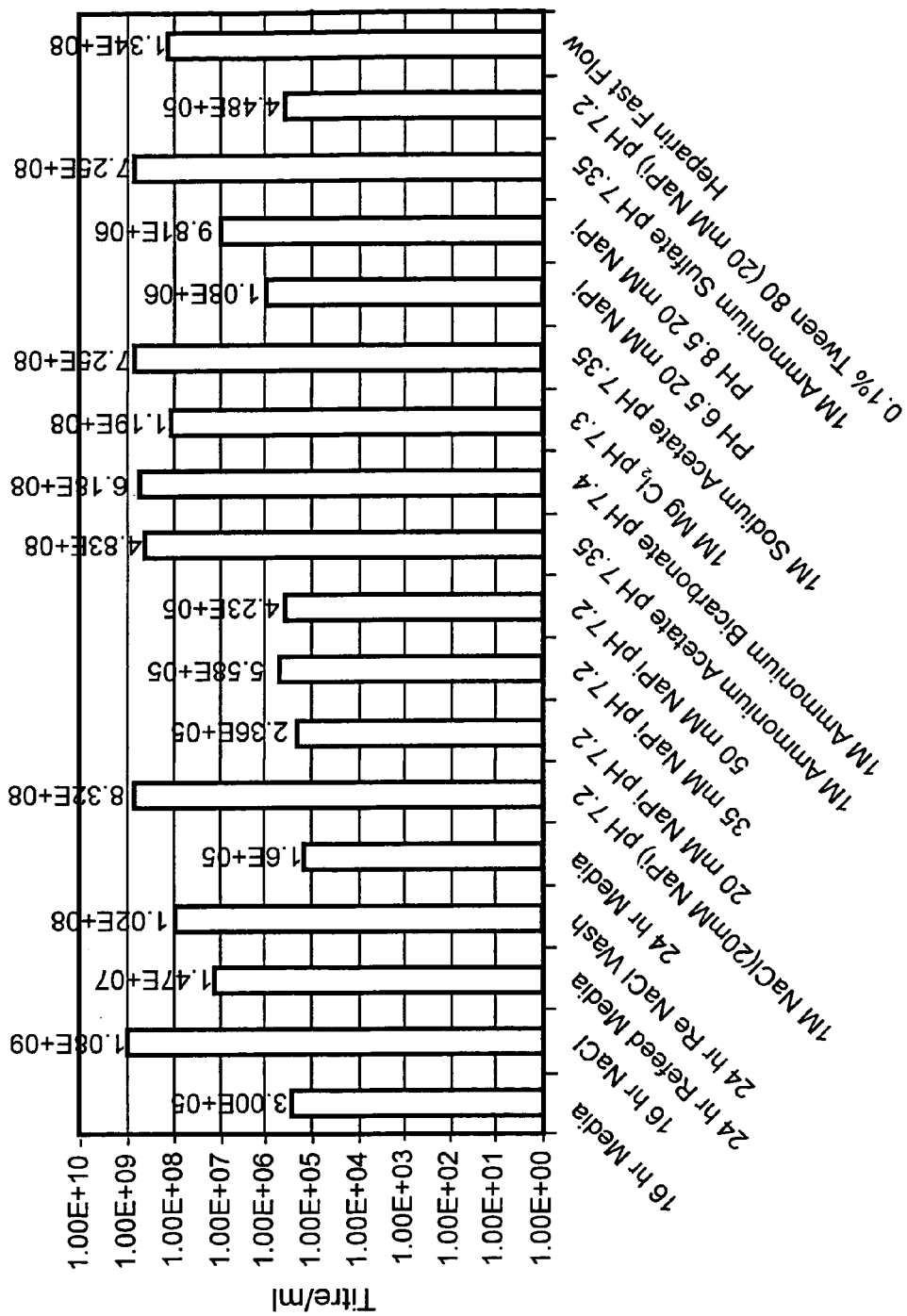
Figure 6:
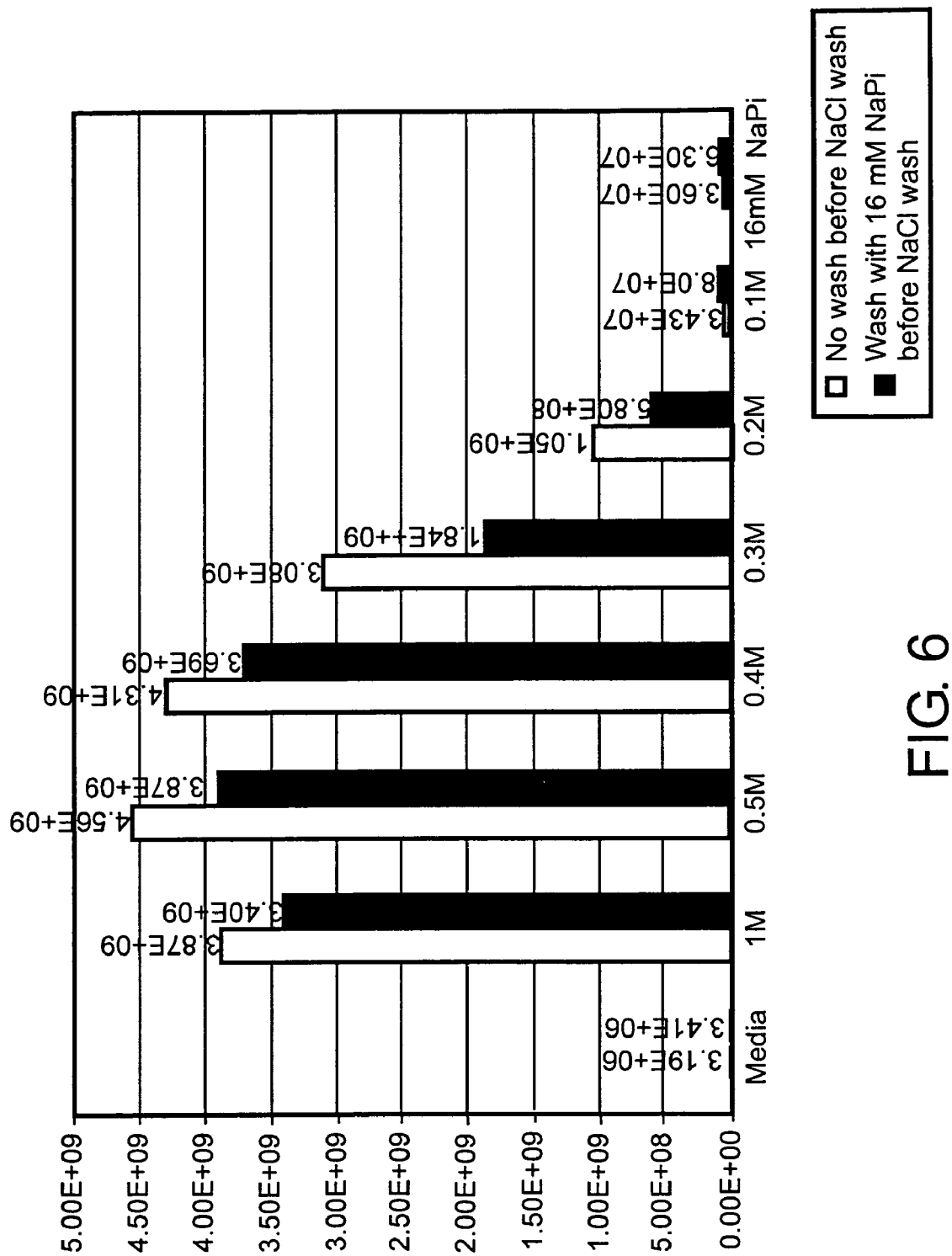

Electroporation was carried out in a 10 mm gap cuvette using $5 \times 10^8$ Vero cells, 150 μg each HIV-gag VEE replicon RNA, VEE capsid helper RNA, and VEE glycoprotein helper RNA. Electroporation was performed using 4 pulses at 1150 V, 25 μF. The electroporated cells were seeded equally among 40 T-75 flasks. One flask was harvested at 16 hours, re-fed with fresh medium and harvested at 24 hours post electroporation. The other flasks were harvested at 24 hours. The media was removed from each flask, and 5 mL of the indicated salt was solution was added to each flask and incubated for five minutes. The salt wash solution was then removed and titered. The results obtained using these different wash solutions are shown in FIG. 5. The amount of ARPs (as measured by titer) released into the growth medium from the cells is mildly affected by pH in the range of pH 7.0–8.0 (see FIG. 3).

B. Salt Concentration in the Release Medium

TABLE 7

Salt Wash Parameters

| NaCl concentration in Release Medium | Temperature (° C.) | ARP Yield |
|---|---|---|
| 5 M | 4 | $3.7 \times 10^8$ |
| 5 M | RT | $4.45 \times 10^8$ |
| 5 M | 37 | $3.5 \times 10^8$ |
| 2.5 M | 4 | $3.1 \times 10^8$ |
| 2.5 M | RT | $3.55 \times 10^8$ |
| 2.5 M | 37 | $4.60 \times 10^8$ |
| 1 M | 4 | $4.05 \times 10^8$ |
| 1 M | RT | $3.75 \times 10^8$ |
| 1 M | 37 | $4.35 \times 10^8$ |
| 0.5 M | 4 | $3.45 \times 10^8$ |
| 0.5 M | RT | $3.84 \times 10^8$ |

Example 10

ARP Purification

ARPs can be purified by affinity chromatography using various resins. Generally, a range of elution conditions can be used, depending on the resin chosen, with care being taken not to subject the ARPs to a pH below approximately 6. It is noted that the antigen encoded by the replicon RNA is usually incorporated within the ARPS; the properties of the antigen can affect the behavior of the ARPs during purification. The skilled artisan knows how to recognize such affects and to modify the ARP purification procedure accordingly.

A. Heparin Affinity Chromatography

ARPs in a salt wash solution are diluted with 5 mM sodium phosphate, pH 7.4, to a sodium chloride content of 0.12 M or less. The solution is then loaded onto a column containing Heparin Sepharose Fast Flow resin (Amersham, Pharmacia Biotech, Inc., Piscataway, N.J.; Catalog No. 17-0998-01) or Heparin HyperD M (Biosepra, Marlboro, Mass.) resin at a linear velocity of 100 cm/hr or less. For example, VEE 3014 ARPs elute at a sodium chloride concentration of approximately 0.3 M at pH 7.4. The VEE 3014 ARPs are collected and formulated by direct dilution or by diafiltration. Typical yields for ARPs purified by this method are 70%. Step or linear salt gradients can be used to elute ARPs.

Most contaminants from serum and from the Vero cells are reduced by the heparin chromatography step; most such contaminants do not bind to the resin.

B. Cellufine Sulfate Affinity Chromatography

ARPs in a salt wash solution are diluted with 5 mM sodium phosphate, pH 7.4, to a sodium chloride content of 0.25 M or less. The solution is then loaded onto a column containing cellufine sulfate resin (Millipore) gradient of increasing sodium chloride content. The ARPs elute at a sodium chloride concentration of approximately 0.7 M at a pH of 7.4. ARPs are collected and formulated by direct dilution or by diafiltration. Typical yields for ARPs purified by this method are 85%.

C. Hydrophobic Interaction Chromatography

ARPs in a salt wash solution are diluted with 5M NaCl/20 mM sodium phosphate pH 7.4 to a final NaCl concentration of 3M. The ARPs are loaded onto a column containing Toyopearl phenyl 650-M resin at a linear velocity of 100 cm/hr and eluted with a linear gradient from 3M to 0M sodium chloride. The recovery of ARPs by this method is approximately 77%.

D. Anion Exchange Chromatography

ARPs are loaded directly, or after suitable dilution, onto anion exchange resin, for example, Toyopearl superQ or Amersham Q Sepharose, or onto anion exchange membranes, for example Mustang Q (Pall Trincor, Exton, Pa.). The Q chromatography materials rely on quaternary amines for binding acidic groups on materials passed over them. The loading conditions are manipulated to provide binding or flow-through of many types of ARPs, with the binding properties being influenced by the expressed protein of interest encoded by the alphavirus replicon vector and expressed in the cells in which the ARPs are produce. In certain cases, the anion exchange resin is sufficient for a single purification step resulting in the reduction of serum proteins, host cell proteins and DNA. The ARP binding properties on a given resin area function of the resin chosen, the ARP species and the pH and salt content of the solution carrying the ARP preparation.

For example, where a Marburg Musoke protein (a glycoprotein) is the encoded antigen of interest and the ARP coat protein is the VEE 3014 coat protein, the ARPs are harvested using the salt wash procedure. The salt wash material (ARP preparation) is loaded directly onto the Mustang Q membrane. Proteins from the salt wash material pass through the membrane, and the membrane is washed with 0.5 M NaCl, 10 mM sodium phosphate to elute any DNA. ARPs are then eluted using a step gradient, with elution at 1.5 M NaCl, 10 mM sodium phosphate.

Example 11

Effect of Different Capsid Helpers

AlphaVax WCB p146 cells were resuspended in PBS to $1.6 \times 10^8$ cell/mL. For electroporations 1–4, the replicon RNA (with Herpesvirus gD coding sequence) was G-capped and purified by size exclusion chromatography. The helper RNAs were uncapped and purified by LiCl precipitation for electroporations 1–3. For electroporation 4, the helper RNAs were uncapped and purified by size exclusion chromatography. 700 µL cells ($1.1 \times 10^8$ cells) were mixed with RNA and electroporated in 0.4 cm cuvettes (BioRad electroporator, 580V, 25 µFd, 4 pulses). Cells were seeded into two T300 cm² flasks with 100 mL OptiPro medium in each. ARPs were harvested about 18 hours post-electroporation in 30 mL 0.5 M NaCl/10 mM NaPO$_4$ and filtered through a 0.2 µm filter.

TABLE 8

RNA Ratio and Capsid Parameters.

| Electroporation | Capsid helper RNA | RNA ratio (in μg) replicon:cap:gp | ARP titer IU/mL | Total IU | IU per cell | Capsid titer IU/mL | gp Titer IU/ |
|---|---|---|---|---|---|---|---|
| 1 | hcap4-3 | 30:30:60 | 1.1e9 | 3.3e10 | 330 | 1.9e5 | 4.9e5 |
| 2 | hcap4 19nt | 30:30:60 | 3.5e8 | 1.1e10 | 110 | 1.1e4 | 2.95 |
| 3 | hcap4 121nt | 30:30:60 | 5.1e8 | 1.5e10 | 150 | 1.2e4 | 3.0e5 |
| 4 | hcap4-3 | 30:100:100 | 3.4e8 | 1.0e10 | 100 | 1.1e4 | 1.7e5 |

What is claimed is:

1. A method for preparing alphaviral replicon particles (ARPS), said method comprising the steps of:
   (a) introducing an alphavirus replicon nucleic acid into a host cell, said replicon nucleic acid comprising at least a virus packaging signal and at least one heterologous coding sequence expressible in said alphaviral replicon nucleic acid, wherein said host cell comprises at least one helper function, to produce a modified host cell;
   (b) culturing said modified host cell under conditions allowing expression of the at least one helper function, allowing replication of said alphaviral replicon nucleic acid and packaging of said alphaviral replicon nucleic acid to form ARPS, wherein said ARPs are heparin-binding ARPS;
   (c) contacting the modified host cells after step (b) with an aqueous solution having an ionic strength of from 0.2 M to 5 M to release the ARPS into the aqueous solution to produce a ARP-containing solution and;
   (d) collecting ARPS from the ARP-containing solution of step (c).

2. The method of claim 1, wherein the at least one helper function in the host cell of step (a) is encoded by a nucleic acid sequence stably integrated within the genome of said host cell.

3. The method of claim 1, wherein the at least one helper function in the host cell is introduced on at least one helper nucleic acid which encodes a capsid protein capable of binding said alphaviral replicon nucleic acid, and at least one alphaviral glycoprotein, wherein said alphaviral glycoprotein associates with said alphaviral replicon nucleic acid and said capsid protein, wherein the at least one helper nucleic acid molecule is introduced into the host cell together with said alphaviral replicon nucleic acid.

4. The method of claim 1, wherein the at least one helper function is encoded by at least two helper nucleic acid molecules wherein each of said two helper nucleic acid molecules encodes at least one viral helper function.

5. The method of claim 1, wherein the ionic strength is between 0.5 M and 5 M.

6. The method of claim 1, wherein the at least one helper function is encoded within a DNA molecule.

7. The method of claim 1, wherein the alphavirus replicon nucleic acid is introduced into said host cell by electroporation.

8. The method of claim 7, wherein host cells are present in an electroporation mixture at a concentration from $5\times10^7$ to $5\times10^8$ per mL.

9. The method of claim 3, wherein host cells are present in an electroporation mixture at a concentration from $5\times10^7$ to $1.5\times10^8$ per mL.

10. The method of claim 1, further comprising a cell washing step, prior to step (c) of claim 1.

11. The method of claim 1, wherein the alphavirus is Venezuelan Equine Encephalitis Virus.

12. The method of claim 10, wherein the cell washing solution contains no salt and further comprises deoxyribonuclease.

13. The method of claim 3 or 4, wherein the helper nucleic acid is an uncapped RNA molecule.

14. The method of claim 4, wherein an alphavirus replicon RNA and a first helper RNA molecule and a second RNA helper molecule are present in an electroporation mixture at a ratio of 1:0.3:0.3 to 1:20:20.

15. The method of claim 14, wherein the ratio is 1:0.5:0.5.

16. The method of claim 14, wherein the ratio is 1:5:5.

17. A method of preparing alphavirus replicon particles comprising introducing an alphavirus replicon vector and one or more helper nucleic acid molecules into alphavirus-permissive cells via electroporation, wherein concentration of the alphavirus permissive cells in culture medium during electroporation is from $5\times10^7$ to $5\times10^8$ cells/mL and wherein the concentration of the alphavirus RNA replicon vector added to the cells prior to electroporation is approximately 35 μg per mL.

18. The method of claim 17, wherein the electroporation is carried out in an electroporation chamber wherein a gap between electrodes is between 0.4 and 1.0 cm.

19. The method of claim 17, wherein the helper function is encoded within a single DNA helper molecule encoding all alphavirus structural proteins.

20. The method of claim 19, wherein the concentration of the DNA helper molecule is at least 100 μg/mL.

21. The method of claim 1, wherein the alphavirus-permissible cells are Vero cells.

22. The method of claim 1, wherein step (d) is followed by an ion exchange, heparin affinity chromatography, affinity or hydrophobic chromatography step.

23. The method of claim 1, wherein the alphavirus is an attenuated alphavirus.

24. The method of claim 17, wherein the alphavirus is Venezuelan equine encephalitis virus (VEE).

25. The method claim 1, wherein the salt in the salt wash step is selected from the group consisting of NaCl, KCl, $MgCl_2$, $CaCl_2$, $NH_4Cl$, $(NH_4)_2SO4$, $NH_4$ acetate and $NH_4$ bicarbonate.

26. A method for preparing alphaviral replicon particles (ARPS), said method comprising the steps of:
   (a) introducing an alphavirus replicon nucleic acid into a host cell, said replicon nucleic acid comprising at least a virus packaging signal and at least one heterologous coding sequence expressible in said alphaviral replicon nucleic acid, wherein said host cell comprises at least one helper function, to produce a modified host cell, wherein said replicon nucleic acid is introduced into the host cell by electroporation of host cells at a concentration of from 5×10 to 5×10 cells per milliliter;

(b) culturing said modified host cell under conditions allowing expression of the at least one helper function, allowing replication of said alphaviral replicon nucleic acid and packaging of said alphaviral replicon nucleic acid to form ARPS;

(c) contacting the modified host cells after step (b) with an aqueous solution having an ionic strength of from 0.2 M to 5 M to release the ARPS into the aqueous solution to produce a ARP containing solution and;

(d) collecting ARPs from the ARP-containing solution of step (c).

27. The method of claim 26, wherein the alphavirus is Venezuelan equine encephalitis virus (VEE).

28. The method of claim 26, wherein the helper nucleic acid is an uncapped RNA molecule.

* * * * *

UNITED STATES PATENT AND TRADEMARK OFFICE
CERTIFICATE OF CORRECTION

| | |
|---|---|
| PATENT NO. | : 7,078,218 B2 |
| APPLICATION NO. | : 10/734609 |
| DATED | : July 18, 2006 |
| INVENTOR(S) | : Jonathan F. Smith et al. |

Page 1 of 1

It is certified that error appears in the above-identified patent and that said Letters Patent is hereby corrected as shown below:

Claim 26, at column 33, line 4:

"from 5×10 to 5×10" should be replaced with --from $5 \times 10^7$ to $5 \times 10^8$--

Signed and Sealed this

Tenth Day of April, 2007

JON W. DUDAS
*Director of the United States Patent and Trademark Office*